United States Patent
Brovold

(10) Patent No.: US 8,825,423 B1
(45) Date of Patent: Sep. 2, 2014

(54) CALIBRATION VERIFICATION

(71) Applicant: Testquip, LLC, Barnes, WI (US)

(72) Inventor: Thomas E. Brovold, Barnes, WI (US)

(73) Assignee: Testquip, LLC, Barnes, WI (US)

( * ) Notice: Subject to any disclaimer, the term of this patent is extended or adjusted under 35 U.S.C. 154(b) by 0 days.

(21) Appl. No.: 14/134,511

(22) Filed: Dec. 19, 2013

(51) Int. Cl.
*G01L 25/00* (2006.01)

(52) U.S. Cl.
CPC ..................................... *G01L 25/00* (2013.01)
USPC .................. 702/85; 702/41; 702/97; 73/1.79; 73/767; 73/783

(58) Field of Classification Search
USPC ........ 702/41–44, 85, 87, 94, 97, 101; 73/760, 73/767, 783, 1.79
See application file for complete search history.

(56) References Cited

U.S. PATENT DOCUMENTS

| | | |
|---|---|---|
| 3,558,866 A | 1/1971 | Poulson |
| 3,983,745 A | 10/1976 | Juusola |
| 4,003,246 A | 1/1977 | Cain |
| 4,841,226 A | 6/1989 | Meline et al. |
| 5,606,515 A | 2/1997 | Mockapetris et al. |
| 5,616,857 A | 4/1997 | Merck, Jr. et al. |
| 5,929,315 A | 7/1999 | Dunegan |
| 5,983,731 A | 11/1999 | Sommerfeld |
| 2006/0070424 A1 | 4/2006 | Saari et al. |
| 2006/0117863 A1 | 6/2006 | Kim |
| 2007/0266572 A1 | 11/2007 | Richter et al. |
| 2008/0134748 A1* | 6/2008 | Hay et al. ........................ 73/1.79 |
| 2009/0019941 A1 | 1/2009 | Sykes |
| 2014/0069203 A1* | 3/2014 | McColskey et al. ............ 73/799 |

OTHER PUBLICATIONS

Wikipedia, "Fracture Toughness," Available Online at en.wikipedia.org/wiki/Fracture_toughness, Jul. 16, 2013, Accessed on Oct. 3, 2013, 7 pages.
Amirkhanian, et al., "Disk-Shaped Compact Tension Test for Concrete," Univ. of Illinois at Urbana-Champaign, 2012, 1 page.
Amirkhanian, et al., "Disk-shaped Compact Tension Test for Plain Concrete," Dept. of Civil Eng., Univ. of Illinois at Urbana-Champaign, 2011, 11 pages.
American Society for Testing and Materials (ASTM), "Designation E 399-90 (Reapproved 1997): Standard Test Method of Plane-strain Fracture Toughness of Metallic Materials," Sep. 30, 2003, 31 pages.
American Society for Testing and Materials (ASTM), "Designation: D 5045-99: Standard Test Methods for Plane-Strain Fracture Toughness and Strain Energy Release Rate of Plastic Materials," Mar. 10, 1999, 9 pages.
ASTM International, "Designation: E 1820-01: Standard Test Method for Measurement of Fracture Toughness," Jun. 10, 2001, 46 pages.
Denneman, "Method to Determine Full Work of Fracture from Disk Shaped Compact Tension Tests on Hot-Mix Asphalt," Proceedings of the 29th Southern African Transport Conference, Aug. 16-29, 2010, 10 pages.

(Continued)

*Primary Examiner* — Manuel L Barbee
(74) *Attorney, Agent, or Firm* — Krenz Hoff, LLP

(57) ABSTRACT

This document generally describes technology to verify the calibration of a materials testing system, such as a compact tension testing system. The calibration of a materials testing system can be verified based on the results generated from the materials testing system running one or more tests on a calibration specimen with one or more known characteristics.

20 Claims, 13 Drawing Sheets

(56) References Cited

OTHER PUBLICATIONS

Donovan, James, "Fracture Toughness Based Models for the Prediction of Power Consumption, Product Size, and Capacity of Jaw Crushers," Dissertation to Virginia Polytechnic Institute and State University, Jul. 2003, 220 pages.
Epsilon Tech, "Model 3541 Fracture Mechanics Clip-On Gages," Available Online at www.epsilontech.com/3541.htm, Accessed on Oct. 3, 2013, 3 pages.
Epsilon Tech, "Model SCM Shunt Calibration Modules," Available Online at www.epsilontech.com/shuntcal.htm, Accessed on Oct. 3, 2013, 2 pages.
Kim et al., Conference paper STRC 2008, "Investigation of fracture toughening mechanisms of asphalt concrete using the clustered discrete element method," 8$^{th}$ Swiss Transport Research Conference, Oct. 15-17, 2008, 32 pages.
Mobasher, et al., "Evaluation of Crack Propagation Properties of Asphalt Mixtures," Journal of Transportation Engineering, Sep./Oct. 1997, 9 pages.
MTS, "Accessories for MTS Criterion™ Systems," Sep. 2012, 64 pages.
MTS, "Clip-On Gages Product Information," 2001-2008, 36 pages.
Pavement Technology Inc. (PTI), "Asphalt Pavement Analyzer (APA) User's Guide," Nov. 4, 2003, 50 pages.
Pinho, Silvestre Taviera, "Fracture Toughness of the Tensile and Compressive Failure Modes in Laminated Composites," Modelling Failure of Laminated Composites Using Physically-Based Failure Models, Chapter 6, Thesis submitted to University of London, 2005, 96 pages.
Strawley, et al., "Experimental Determination of the Dependence of Crack Extension force on Crack Length for a Single-Edge-Notch Tension Specimen," NASA Technical Note TN D-2396, Aug. 1964, 23 pages.
Varadarajan, et al., "Compliance calibration for fatigue crack propagation testing of ultra high molecular weight polyethylene," Biomaterials, 27, Mar. 17, 2006, 5 pages.
Vial, Gilbert, "Tech Spotlight: Video Extensometers," Advanced Materials & Processes, Apr. 2004, 2 pages.
Wagoner, et al., "Disk-shaped Compact Tension Test for Asphalt Concrete Fracture," Society for Experimental Mechanics, vol. 45, No. 3, Jun. 2005, 8 pages.
Wagoner, et al., "Investigation of the Fracture Resistance of Hot-Mix Asphalt Concrete Using a Disk-Shaped Compact Tension Test," Transportation Research Record: Journal of the Transportation Research Board, No. 1929, 2005, 10 pages.
Wikipedia, "Extensometer," Available Online at en.wikipedia.org/wiki/Extensometer, Jun. 1, 2013, Accessed on Oct. 7, 2013, 4 pages.
"Direct Tension Tester|Asphalt Test, Equipment Binder Testing," [online], http://www.interlaken.com/soilandasphalt/direct_tension.html, dated Jul. 23, 2014, as retrieved from archive.org on May 30, 2014, 5 pages.

* cited by examiner

CALIBRATION VERIFICATION

TECHNICAL FIELD

This document generally describes technology to verify one or more calibrations of materials testing systems.

BACKGROUND

Materials testing systems, such as compact tension testing systems and tensile strength testing systems, have included devices to make various measurements related to materials under examination during a testing process. For example, a compact tension testing system can include a load measurement device to measure an amount of force (stress) exerted on a material specimen and a distance measurement device to measure the displacement (strain) of the material specimen as the load is applied to the specimen. To ensure the accuracy of measurements, such devices have been calibrated on a period basis (e.g., annually) by a technician against a verified sample with the assumption that the calibration of these devices will not drift more than an acceptable amount between calibrations.

SUMMARY

This document generally describes technology to verify the calibration of a materials testing system, such as a compact tension testing system. The calibration of a materials testing system can be verified based on the results generated from the materials testing system running one or more tests on a calibration specimen with one or more known characteristics. For example, a calibration specimen with a known energy characteristic can be tested by a materials testing system to obtain measurements for an amount of displacement in the calibration specimen in response to a load applied to the calibration specimen. Such measurements can be used to determine an amount of energy exerted and detected by the materials testing system, which can be compared against the known energy characteristic for the calibration specimen to determine whether the materials testing system is properly calibrated.

In one implementation, a method for verifying calibration of a materials testing system includes: obtaining first information that indicates, at least, an energy characteristic of a calibration specimen, the energy characteristic defining a relationship between force and distance for the calibration specimen, wherein the calibration specimen is made of a material with at least a threshold level of elasticity; receiving, at a computational unit, results from a test run on the calibration specimen by the materials testing system, wherein the results are based on force and distance measurements taken by the materials testing system during the test, the test applying one or more loads to the calibration specimen that are within an elastic region of the material of the calibration specimen; determining, by the computational unit, whether one or more measurement devices of the materials testing system are calibrated within a threshold tolerance based on a comparison of (i) the energy characteristic of the calibration specimen and (ii) the results of the test run on the calibration specimen by the materials testing system; and outputting, by the computational unit, second information that indicates whether the one or more measurement devices of the materials testing system are calibrated within the threshold tolerance.

Such a method can optionally include one or more of the features described in the following paragraphs, which may be used together in various combinations, as appropriate. The one or more measurement devices can include, at least, a distance measuring device. The first information can further identify distances for a plurality of fixed-distance spans. The method can further include receiving distance measurements taken by the distance measuring device for the plurality of fixed-distance spans; determining a correction to apply to measurements taken by the distance measuring device based on a comparison of (i) the distances for the plurality of fixed-distance spans and (ii) the distance measurements taken by the distance measuring device for the plurality of fixed-distance spans; and outputting the correction for the distance measuring device. The comparison of (i) the distances for the plurality of fixed-distance spans and (ii) the distance measurements taken by the distance measuring device for the plurality of fixed-distance spans can include a comparison of (iii) one or more differences between the distances for the plurality of fixed-distance spans and (iv) one or more differences between the distance measurements taken by the distance measuring device for the plurality of fixed-distance spans. The fixed-distance spans can be defined by physical elements that are affixed to or embedded within one or more surfaces of the calibration specimen. The distance measuring device can be a contact distance measuring device. The distance measuring device can be a crack mouth opening displacement (CMOD) gauge. The distance measuring device can be a non-contact distance measuring device. The method can further include adjusting, based on the correction for the distance measuring device, the results from the test run on the calibration specimen by the materials testing system to generate adjusted results, where the determination of whether the one or more measurement devices are calibrated within the threshold tolerance is based on a comparison of (i) the energy characteristic of the calibration specimen and (ii) the adjusted results. The fixed distance spans can be formed on one or more devices that are separate from the calibration specimen. The correction for the distance measuring device can include one or more adjustments to distance measurements that are taken by the distance measuring device. The one or more adjustments can be linear adjustments to the distance measurements.

The test run on the calibration specimen by the materials testing system can be performed while the materials testing system is in an operational mode of operation during which the materials testing system is configured to test material specimens, the operational mode being different from a calibration mode of operation during which one or more components of the materials testing system are altered from their state during the operational mode.

The elastic region of the material can include a range that is bounded by a threshold value before yield point for the material.

The method can further include determining, based on the determination of whether the one or more measurement devices of the materials testing system are calibrated within the threshold tolerance, one or more corrections to measurements made by the one or more measurement devices; and outputting the one or more corrections for the one or more measurement devices. The one or more corrections can include one or more adjustments to force measurements that are taken by the materials testing system with regard to the load that is applied by the materials testing system. The method can further include receiving, by the computer system, production results from a test run on a viscoelastic material by the materials testing system; adjusting, based on the one or more corrections, the production results to generate adjusted production results; and outputting, by the computer system, the adjusted production results for the viscoelastic material. The one or more corrections can include one or more adjustments to force measurements that are taken by the materials testing system with regard to the load that is applied by the materials testing system. The one or more adjustments can be linear adjustments to the force measurements. The viscoelastic material can be asphalt.

The materials testing system can include a machine to perform disc-shaped compact tension (DCT) tests, a load measurement device to measure loads applied to the calibration specimen by the machine, and a distance measuring device. The computational unit can include a computer system. The computer system can be part of the materials testing system.

The materials testing system can include a machine to perform tensile strength tests, a load measurement device to measure loads applied to the calibration specimen by the machine, and a distance measuring device.

In another implementation, an apparatus for verifying calibration of a materials testing system can include a calibration specimen that sized and shaped to be fitted into the materials testing system for application of one or more loads; a first pair of physical elements that define a first span across a portion of the calibration specimen that, as the one or more loads are applied to the calibration specimen by the materials testing system, will have a variable distance; and a plurality of second pairs of physical elements that define a plurality of second spans across portions of the calibration specimen that have fixed-distances.

Such an apparatus can include one or more of the features described in the following paragraphs, which may be used together in various combinations, as appropriate. Each of the plurality of second pairs of physical elements can have distances that are distinct. The calibration specimen can be made of a metallic material. The metallic material can be aluminum. One of the plurality of second pairs of opposing edges defines a distance that can be the same or similar to a first distance defined by the first pair of opposing edges when no load is applied to the calibration specimen by the materials testing system. Another of the plurality of second pairs of opposing edges can define a distance that is greater than the first distance. Another of the plurality of second pairs of opposing edges can define a distance that is less than the first distance. The calibration specimen can include a crack that extends through a first dimension of the calibration specimen and, along a second dimension of the calibration specimen, extends from an interior point within the calibration specimen to a crack mouth opening at a surface of the calibration specimen, and the first span can overlap at least part of the opening. The plurality of second pairs of opposing edges can be defined by pairs of material blocks that are affixed to one or more surfaces of the calibration specimen. The one or more surfaces to which the pairs of material blocks are affixed can be different from a surface of the calibration specimen at which the first pair of opposing edges is located. The plurality of second pairs of opposing edges can be defined by grooves, holes, or voids within one or more surfaces of the calibration specimen.

The calibration specimen can include a front surface; a back surface that is substantially parallel to the front surface; first and second internal circular sidewalls that extend from the front surface to the back surface creating first and second voids that pass through the calibration specimen, the first and second voids being sized and shaped to engage testing arms for the materials testing machine; a top surface that is substantially perpendicular to the front and back surfaces, the top surface being bifurcated by internal linear sidewalls that are substantially perpendicular to the top surface, the front surface, and the back surface, the internal linear sidewalls extending from the front surface to the back surface creating a crack that passes from the top surface to an internal point of termination that is located between the top surface and a bottom surface; and a semi-circular sidewall that, at one end, engages a first of the internal linear sidewalls and, at its other end, engages a second of the internal linear sidewalls at or near the internal point of termination of the crack, the semi-circular sidewall extending perpendicularly from the front surface to the back surface to create an circular void that extends through the calibration specimen at an end of the crack. A diameter of the circular void, a length of the crack, a bottom distance from the circular void to the bottom surface, and a width of the calibration specimen can be particularly dimensioned so as to provide, within a threshold tolerance, parity between a measured percentage change in displacement and a measured percentage change in force as a load is applied to the calibration specimen by the materials testing machine. The length of the crack can be greater than the width of the calibration specimen, the diameter of the circular void, and the bottom distance; the width of the calibration specimen can be greater than the diameter of the circular void, and the bottom distance; and the bottom distance can be greater than the diameter of the circular void. The length of the crack can be between 4.0 inches and 4.5 inches, inclusive; the diameter of the circular void can be between 0.4 inches and 0.9 inches, inclusive; the bottom distance can be between 0.6 inches and 1.25 inches, inclusive; and the width of the calibration specimen can be between 3.25 and 4.25 inches, inclusive.

In another implementation, a system for determining whether a materials testing system is calibrated can include a calibration specimen that is sized and shaped for testing by the materials testing system, the calibration specimen being made of a material with at least a threshold level of elasticity; and a computational unit that is programmed to: i) receive results from a test run on the calibration specimen by the materials testing system, ii) determine, based on a comparison of the results and an energy characteristic for the calibration specimen, whether the materials testing system is calibrated within a threshold tolerance, and iii) output information that indicates whether the materials testing system is calibrated within the threshold tolerance, where the energy characteristic defines a relationship between force and distance for the calibration specimen.

Such a system can include one or more of the features described in the following paragraphs, which may be used together in various combinations, as appropriate. The system can further include a plurality of pairs of physical elements that define a plurality of fixed-distance spans, where the computational unit can be further programmed to determine a correction to apply to measurements taken by a distance measuring device of the materials testing system based on a comparison of (i) known distances for the plurality of fixed-distance spans and (ii) the distance measurements taken by the distance measuring device for the plurality of fixed-distance spans. The computational unit can be further programmed to modify the results from the test run on the calibration specimen by the materials testing system based on the correction, and to determine of whether the materials testing system is calibrated based on the modified results. The computational unit can be a computer system. The computer system can be part of the materials testing system.

The computational unit can further be programmed to receive distance measurements taken by a distance measuring device for a plurality of fixed-distance spans; determine a correction to apply to measurements taken by the distance measuring device based on a comparison of (i) known distances for the plurality of fixed-distance spans and (ii) the distance measurements taken by the distance measuring device for the plurality of fixed-distance spans; and output the correction for the distance measuring device. The comparison of (i) the distances for the plurality of fixed-distance spans and (ii) the distance measurements taken by the distance measuring device for the plurality of fixed-distance spans can include a comparison of (iii) one or more differences between the distances for the plurality of fixed-distance spans and (iv) one or more differences between the distance measurements taken by the distance measuring device for the plurality of fixed-distance spans. The fixed-distance spans can be defined by physical elements that are affixed to or embedded within one or more surfaces of the calibration specimen. The distance measuring device can be a contact distance measuring device. The distance measuring device can be a crack mouth opening displacement (CMOD) gauge. The distance measuring device can be a non-contact distance measuring device. The computational unit can further be programmed to adjust, based on the correction for the distance measuring device, the results from the test run on the calibration specimen by the materials testing system to generate adjusted results, where the determination of whether the one or more measurement devices are calibrated within the threshold tolerance is based on a comparison of (i) the energy characteristic of the calibration specimen and (ii) the adjusted results. The fixed distance spans can be formed on one or more devices that are separate from the calibration specimen. The correction for the distance measuring device can include one or more adjustments to distance measurements that are taken by the distance measuring device. The one or more adjustments can be linear adjustments to the distance measurements.

The test run on the calibration specimen by the materials testing system can be performed while the materials testing system is in an operational mode of operation during which the materials testing system is configured to test material specimens, the operational mode being different from a calibration mode of operation during which one or more components of the materials testing system are altered from their state during the operational mode.

The elastic region of the material can include a range that is bounded by a threshold value before yield point for the material.

The computational unit can further be programmed to determine, based on the determination of whether the one or more measurement devices of the materials testing system are calibrated within the threshold tolerance, one or more corrections to measurements made by the one or more measurement devices; and output the one or more corrections for the one or more measurement devices. The one or more corrections can include one or more adjustments to force measurements that are taken by the materials testing system with regard to the load that is applied by the materials testing system. The computational unit can further be programmed to receive production results from a test run on a viscoelastic material by the materials testing system; adjust, based on the one or more corrections, the production results to generate adjusted production results; and output the adjusted production results for the viscoelastic material. The one or more corrections can include one or more adjustments to force measurements that are taken by the materials testing system with regard to the load that is applied by the materials testing system. The one or more adjustments can be linear adjustments to the force measurements. The viscoelastic material can be asphalt.

The materials testing system can include a machine to perform disc-shaped compact tension (DCT) tests, a load measurement device to measure loads applied to the calibration specimen by the machine, and a distance measuring device. The computational unit can include a computer system. The computer system can be part of the materials testing system.

The materials testing system can include a machine to perform tensile strength tests, a load measurement device to measure loads applied to the calibration specimen by the machine, and a distance measuring device In another implementation, a method for verifying calibration of a materials testing system includes: obtaining information that indicates, at least, an energy characteristic of a calibration specimen, the energy characteristic defining a relationship between force and distance for the calibration specimen, wherein the calibration specimen is made of a material with at least a threshold level of elasticity; receiving, at a computer system, results from a test run on the calibration specimen by the materials testing system, wherein the results include force and distance measurements taken by the materials testing system during the test, the test applying one or more loads to the calibration specimen that are within an elastic region of the material of the calibration specimen; determining, by the computer system, one or more corrections to one or more measurement devices of the materials testing system based on a comparison of (i) the energy characteristic of the calibration specimen and (ii) the results of the test run on the calibration specimen by the materials testing system; and outputting, by the computer system, the one or more corrections for use modifying measurements from the one or more measurement devices of the materials testing system.

Such a method can include one or more of the features described in the following paragraphs, which may be used together in various combinations, as appropriate. The one or more measurement devices includes, at least, a distance measuring device. The information can further identify distances for a plurality of fixed-distance spans. The method can further include receiving, at the computer system, distance measurements taken by the distance measuring device for the plurality of fixed-distance spans; determining, by the computer system, a correction to apply to measurements taken by the distance measuring device based on a comparison of (i) the distances for the plurality of fixed-distance spans and (ii) the distance measurements taken by the distance measuring device for the plurality of fixed-distance spans; and outputting, by the computer system, the correction for the distance measuring device. The comparison of (i) the distances for the plurality of fixed-distance spans and (ii) the distance measurements taken by the distance measuring device for the plurality of fixed-distance spans can include a comparison of (iii) one or more differences between the distances for the plurality of fixed-distance spans and (iv) one or more differences between the distance measurements taken by the distance measuring device for the plurality of fixed-distance spans. The fixed-distance spans can be affixed to or embedded within one or more surfaces of the calibration specimen. The fixed-distance spans can be formed on one or more devices that are separate from the calibration specimen. The distance measuring device can include a crack mouth opening displacement (CMOD) gauge. The method can further include adjusting, based on the correction for the distance measuring device, the results from the test run on the calibration specimen by the materials testing system to generate adjusted results, where the one or more corrections to the one or more measurement devices is determined based on a comparison of (i) the energy characteristic of the calibration specimen and (ii) the adjusted results. The correction for the distance measuring device can include one or more adjustments to distance measurements that are taken by the distance measuring device. The one or more adjustments can be linear adjustments to the distance measurements.

The test run on the calibration specimen by the materials testing system can be performed while the materials testing system is in an operational mode and configuration during which material specimens are tested, the operational mode and configuration being different from a calibration mode and configuration during which one or more components of the materials testing system are altered from their state during the operational mode and configuration. The elastic region of the material includes a range that can be bounded by a threshold value before yield point for the material.

The method can further include receiving second results from a second test run on the calibration specimen by the materials testing system; adjusting, based on the one or more corrections, the second results to generate adjusted second results; and verifying, by the computer system, the second results based on a comparison of the adjusted second results and the energy characteristic of the calibration specimen. The materials testing system can be a machine to perform disc-shaped compact tension (DCT) tests, a load measurement device to measure loads applied to the calibration specimen by the machine, and a distance measuring device. The materials testing system can be a machine to perform tensile strength tests, a load measurement device to measure loads applied to the calibration specimen by the machine, and a distance measuring device.

The one or more corrections can include one or more adjustments to force measurements that are taken by the materials testing system with regard to the load that is applied by the materials testing system. The one or more adjustments can be linear adjustments to the force measurements.

The method can further include receiving, by the computer system, production results from a test run on a viscoelastic material by the materials testing system; adjusting, based on the one or more corrections, the production results to generate adjusted production results; and outputting, by the computer system, the adjusted production results for the viscoelastic material. The viscoelastic material can be asphalt. The calibration specimen can be made of a metallic material. The metallic material can be aluminum.

In another implementation, a calibration specimen for verifying calibration of a disk-shaped compact tension (DCT) test machine includes a front surface; a back surface that is substantially parallel to the front surface; first and second internal circular sidewalls that extend from the front surface to the back surface creating first and second voids that pass through the calibration specimen, the first and second voids being sized and shaped to engage testing arms for the DCT test machine; a top surface that is substantially perpendicular to the front and back surfaces, the top surface being bifurcated by internal linear sidewalls that are substantially perpendicular to the top surface, the front surface, and the back surface, the internal linear sidewalls extending from the front surface to the back surface creating a crack that passes from the top surface to an internal point of termination that is located between the top surface and a bottom surface; and a semi-circular sidewall that, at one end, engages a first of the internal linear sidewalls and, at its other end, engages a second of the internal linear sidewalls at or near the internal point of termination of the crack, the semi-circular sidewall extending perpendicularly from the front surface to the back surface to create an circular void that extends through the calibration specimen at an end of the crack, where a diameter of the circular void, a length of the crack, a bottom distance from the circular void to the bottom surface, and a width of the calibration specimen are particularly dimensioned so as to provide, within a threshold tolerance, parity between a measured percentage change in displacement and a measured percentage change in force as a load is applied to the calibration specimen by the DCT test machine.

Such a calibration specimen can include one or more of the features described in the following paragraphs, which may be used together in various combinations, as appropriate. The length of the crack can be greater than the width of the calibration specimen, the diameter of the circular void, and the bottom distance; the width of the calibration specimen can be greater than the diameter of the circular void, and the bottom distance; and the bottom distance can be greater than the diameter of the circular void. The length of the crack can be between 4.0 inches and 4.5 inches, inclusive; the diameter of the circular void can be between 0.4 inches and 0.9 inches, inclusive; the bottom distance can be between 0.6 inches and 1.25 inches, inclusive; and the width of the calibration specimen can be between 3.25 and 4.25 inches, inclusive. The calibration specimen can be made of a material that includes aluminum.

The details of one or more implementations are depicted in the associated drawings and the description thereof below. Certain implementations may provide one or more advantages. For example, the calibration of a materials testing system can be verified in a more efficient and cost effective manner. Materials testing system have traditionally been calibrated through the use of a specially-trained technician physically travelling to a client's site, physically transforming the materials testing system from an operational mode to a calibration mode of operation (e.g., removing arms that hold testing specimens), and calibrating the output of one or more measurement devices of the materials testing system against verified calibration tools. Such procedures can be expensive (e.g., travel and labor costs for a specially trained technician using verified calibration tools) and time intensive (e.g., one day or more of time for a technician to complete calibration).

The disclosed technology in this document allow for calibration of a materials testing system to be determined more efficiently and cost effectively through the use of calibration specimens. Instead of having a technician travel to a site and modify a materials testing system for calibration, a calibration specimen can be tested in the materials testing systems and, based on the results of that test, can provide an indication of whether the materials testing system is properly calibrated. Such a calibration verification test can be performed on a routine basis (e.g., daily) in a short amount of time (e.g., 5-10 minutes), in contrast to the technician-based calibration which is generally performed once a year and can take a day or more for a technician to perform.

In another example, the results produced by a materials testing system can be validated as correct during periods of time between calibrations. Calibrations of materials testing systems have been performed on an infrequent basis (e.g., once a year), which has resulted in users of materials testing systems having to blindly assume that the calibration of their materials testing system was still properly calibrated in the period between calibrations. However, materials testing systems can fall out of calibration over time, which can lead to results for material samples that are under test that, unbeknownst to the user, are erroneous. For instance, for a materials testing system that is on a schedule to be calibrated each year on February 1, a user of that materials testing system would have no way to verify that the materials testing system is still calibrated (and has not fallen out of calibration) when performing tests from February 2 to January 31 the next year—an assumption would have to be made as to the validity of the calibration of the materials testing system. During that time, the materials testing system could have fallen out of calibration and could be producing invalid test results, but the user would have no way of knowing it. Additionally, this problem can be compounded when different materials testing systems are producing different results for material specimens that should be producing the same or similar test results—it is unclear which of the materials testing systems is properly calibrated and producing the correct results, if any, and which are not.

The disclosed technology allows for a user to readily verify the calibration of a materials testing system and the results that the materials testing system is producing between calibrations. For instance, by running a verification test on a calibration specimen, as described in greater detail below, an indication can be provided as to whether a materials testing system is still properly calibrated. After determining that a materials testing system is still properly calibrated, such as 6 or 9 months after a previous calibration, the results generated for materials under test by the materials testing system can be verified as being correct (e.g., within a threshold tolerance value). Such verifications using the disclosed technology can eliminate the guess work and assumptions that are baked into test results that are generated in periods between calibrations for a materials testing system. Additionally, such verifications can be used to readily identify which, of a plurality of materials testing systems, are properly calibrated and producing correct test results.

In a further example, calibration verification can be performed with regard to both distance measuring devices and load measuring devices, and can discern between test results that provide correct and false indications of calibration. For instance, a materials testing system that is using a distance measuring device that is producing distance measurements that are off by −5% and that is using a load measuring device that is producing load measurements that are off by +5%, may provide results that provide an indication of proper calibration based on the errors in the measuring devices offsetting each other. In such a situation, performing calibration verification with regard to only one of these two measuring devices may not identify that the materials testing system is not properly calibrated (may provide a false indication of calibration). By performing calibration verification with regard to both the distance and load measuring devices, a correct indication that the materials testing system is not properly calibrated can be generated, which can provide for more robust and accurate calibration verifications.

In another example, calibration specimens that are used as part of the calibration verification can be designed with particular dimensions that provide near parity between percentage change in displacement and the percentage change in load when performing calibration verification tests. Such near parity can provide a greater level of granularity and accuracy when determining whether a materials testing system is properly calibrated.

In a further example, calibration verification tests can be performed while a materials testing system is in an operational mode instead of in a calibration mode of operation, which can provide a more accurate indication of whether tests results that are produced during the operational mode are based on a proper calibration of the materials testing system. Modifying a materials testing system, such as removing arms that engage a material specimen, to be in a calibration mode of operation can introduce differences that may not be accounted for during calibration but which may cause variations in test results. By performing calibration verification tests while a materials testing system in an operational mode, the test results that are generated by a materials testing system can be validated without making assumptions that the delta between the calibration mode of operation and the operational mode do not introduce any additional variance.

In another example, calibration verification can be performed accurately by testing calibration specimens in a materials testing system against one or more characteristics of materials that compose the calibration specimens. For instance, by using differences (e.g., percentage change) in displacement and load during a test of a calibration specimen, the differences can be used to determine an amount of energy exerted on the calibration specimen during the calibration test. Such an amount of energy can be compared to an energy characteristic for the calibration specimen to identify whether the determined amount of energy generated by the materials testing system and its current calibration is consistent with the energy characteristic for the calibration specimen.

Other features, objects, and advantages of the technology described in this document will be apparent from the description and the drawings, and from the claims.

BRIEF DESCRIPTION OF THE DRAWINGS

Like reference symbols in the various drawings indicate like elements.

DETAILED DESCRIPTION

Figure 1:
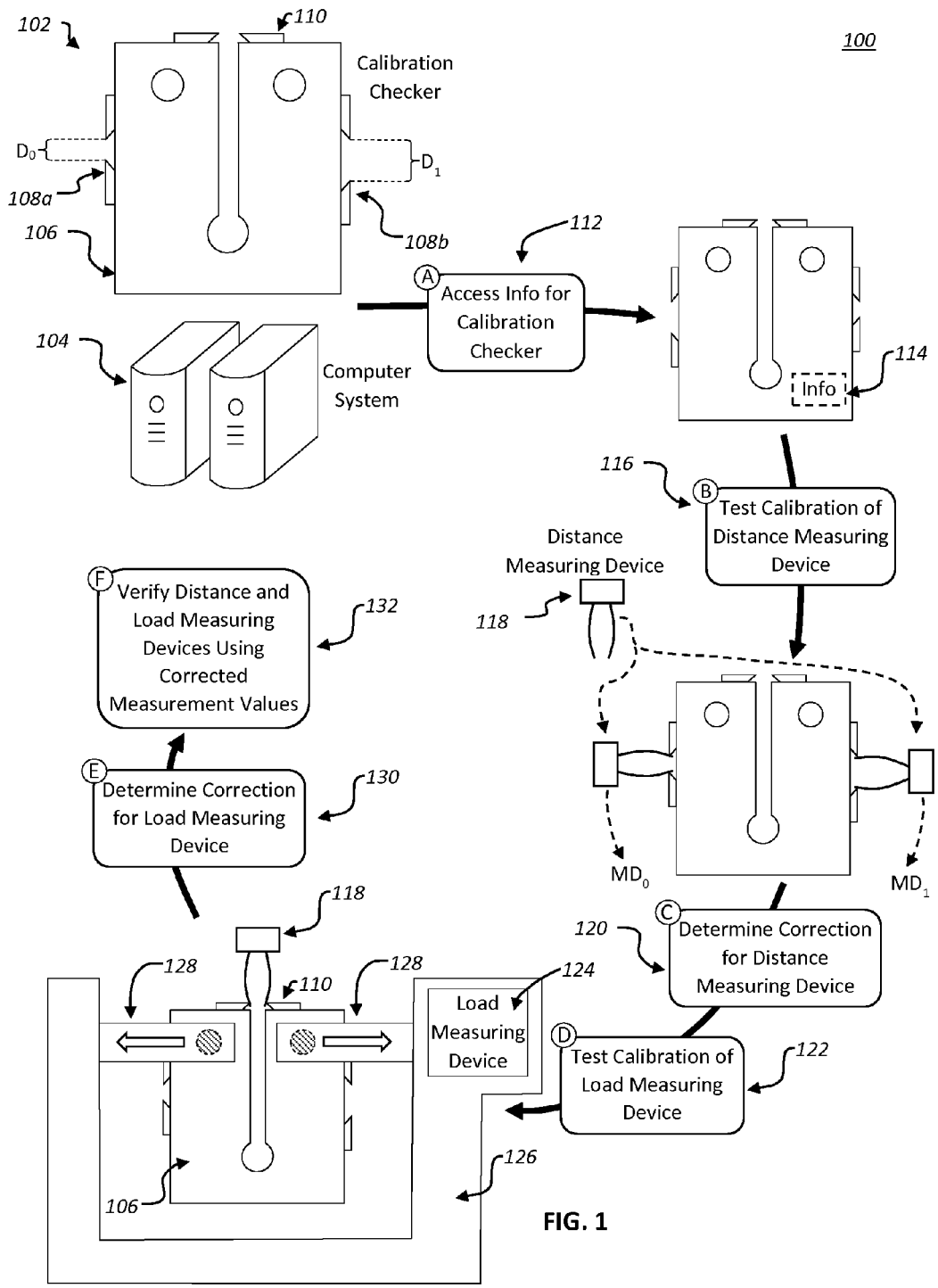
FIG. 1 is a conceptual diagram of an example system for checking calibrations of a materials testing system.

Materials testing systems, such as compact tension testing systems and tensile strength testing systems, typically need to be calibrated at regular intervals, such as once a year, to ensure proper performance when testing materials. Many testing systems test materials with regard to force that is applied to materials under test and a resulting displacement or strain (e.g., a displacement provided as a percentage of a length) that results in the specimen as a result of the applied force. Such variables (force, displacement, strain) can be measured to characterize the material or structure that is being tested by a materials testing system. Improperly calibrated materials testing systems can introduce a variety of problems, such as incorrectly characterizing materials with defects as being free from defects and vice versa, which can mislead engineers and designers who may rely on such test results, such as to produce products. For instance, relationships derived from force and displacement measurements provided by a materials testing system can be used for quality control and quality assurance of products that use a material under test. A materials testing system with that is out of calibration can incorrectly represent such relationships and, as a result, can report false positives (e.g., results that erroneously indicate that a material under test is within an acceptable range of quality as indicated by a force/displacement relationship) and false negatives (e.g., results that erroneously indicate that a material under test is outside of an acceptable range of quality as indicated by a force/displacement relationship).

Calibrations can be expensive and time consuming, often using the services of a trained technician who physically travels to the site of a materials testing system and uses a validated calibration source to perform calibrations. Accordingly, many users allow for longer intervals between calibrations, such as calibrations on an annual basis. In the time between calibrations, such as six months after a previous calibration, users of materials testing systems may have no idea whether their materials testing system is still calibrated or, instead, has drifted from its previous calibration and is now producing erroneous test results. Users are left to assume whether or not their materials testing system is still properly calibrated in intervals between calibrations. However, such assumptions can call into question the validity of any and all results that are generated by materials testing systems.

Through the use of calibration checkers described in this document, the calibration of materials testing systems can be verified in fast, reliable, easy to perform, and inexpensive procedures that can determine whether a materials testing system is calibrated properly. Such procedures can indicate whether a materials testing system is properly calibrated instantly, and without calling and waiting for a costly calibration to provide assurance as to the calibration of the materials testing system. Such a calibration checker can include a calibration specimen that exhibits a reliable and repeatable relationship between force and displacement (or strain) for measurement by a materials testing system. Such calibration checkers can allow for the results from two measurements to be taken simultaneously, which and provide an immediate indication as to whether the stress versus strain measurements from a materials testing system are reliable and accurate, and whether the materials testing system is properly calibrated. This is in contrast to other devices, such as a proving ring, which may only measure force and not displacement or strain, which may have to be measured at a different time during a separate operation and test setup.

The calibration of a materials testing system can be checked by running a test on a calibration specimen using the materials testing system to measure force and displacement of the calibration specimen during the test. A calibration specimen can have a general shape that is similar to the shape of specimens for which materials testing systems are designed (e.g., a calibration specimen for a compact tension testing system can be similar in shape to materials specimens that are tested by the compact tension testing system), but may have particular dimensions that are different from those of a standard specimen for such a machine. The dimensions and/or material of a calibration specimen can be selected to allow for tests run on the calibration specimen to include the application of at least a threshold level of force to the calibration specimen so as to sufficiently test the materials testing system while still being within an elastic region for the calibration specimen. The elastic region for a calibration specimen can include a range of force that is a threshold value less than a yield point for the material such that, when a load within the range of force is applied to and then removed from the calibration specimen, the calibration specimen returns to its original shape and dimensions.

Tests on a calibration specimen by a materials testing system can include applying a load to the calibration specimen while measuring the force and displacement of the specimen. The force and displacement measurements can be used to determine a level of energy stored by the calibration specimen during the test. For example, the level of energy stored by the calibration specimen can be determined by plotting the force against the displacement and measuring the area under a curve that provides the measured relationship between force and displacement for the calibration specimen. Such a determination of the measured energy in the calibration specimen can be compared against a known energy characteristic for the calibration specimen (each calibration checker can include information that, either directly or indirectly, provides an energy characteristic for a calibration specimen that is part of the calibration checker). If a measured energy level is within a threshold tolerance (e.g., +/−1%, +/−2%, +/−5%) of an energy characteristic for a calibration specimen, then the materials testing system that is being evaluated and from which the measured energy levels were derived can be determined to be properly calibrated. In contrast, if the measured energy levels is not within a threshold tolerance of an energy characteristic, then a materials testing system that is being evaluated can be determined to not be properly calibrated. A degree to which a materials testing system is not properly calibrated, such as a percentage difference between a measured energy level and an energy characteristic for a calibration specimen, can also be determined.

A calibration checker can reliably and consistently respond to tests that are run by different materials testing systems and/or at different times so as to provide a reliable benchmark against which the calibration of the materials testing systems can be judged. For example, when tested in across different materials testing systems, the same calibration checker will generate the same (or similar within a threshold tolerance) energy measurement by each of the different materials testing systems so long as each of the different materials testing systems are properly calibrated. If one the materials testing systems produces a measure of energy that is different from measures of energy for the other materials testing systems, then at least one of the materials testing system is not properly calibrated. Similarly, the same calibration checker can be used to test the same materials testing system frequently (e.g., daily, weekly, before each test of a materials specimen, after every 10 tests of materials specimens) in between calibrations of the materials testing system (e.g., in between annual calibrations), which can provide indications as to whether the materials testing system has gone out of calibration in between such calibrations. If a materials testing system is determined to have gone out of calibration, such a determination can provide a user of the materials testing with an indication that the results generated by the materials testing system are no longer reliable and can prompt the user to set-up another in-person calibration with a technician.

Testing the calibration of a materials testing system using energy measurements can provide a true representation of the accuracy of the calibrations of materials testing systems. For example, if the load measured by a materials testing system is less than the actual load (e.g., load measurements are off by −10%), the resulting strain/displacement measurement will be higher (e.g., strain measurement off by +10%) based on the calibration specimen having strained according to the actual load, which was more than the measured load. In such a situation, the energy measured for the test would be greater than the actual energy for the test (e.g., energy measurement off by +10%) and such an energy measurement would provide an indication that the materials testing system is out of calibration.

However, if one of the load or strain/displacement measurement devices (e.g., load or strain transducers) measures a value that is greater than the actual load or strain/displacement and the other measures a value that is greater by the same amount, the resulting energy measurement would appear to be correct (even though it is inaccurate) based on the error in the load and strain/displacement measurement devices offsetting each other. As described in greater detail below, such a false indication of a correct calibration of a materials testing system can be avoided by first determining whether one of the measuring devices is correctly calibrated before determining whether other measuring devices are correctly calibrated. For example, the calibration of a strain/displacement measuring device can first be tested using two or more pairs of gauge points that have known differences in distance (e.g., first pair of gauge points has a distance of 2.0 mm and second pair of gauge points has a distance of 3.0 mm for a difference of 1.0 mm). Measurements for each of the first and second pairs of gauge points can be taken using the strain/displacement measuring device, the difference between the measurements can be determined, and the difference can be compared against the known difference between the first and second pairs of gauge points. For instance, if the known difference between the distance of the first and second pair of gauge points 1.0 mm (e.g., first pair are 2.0 mm apart and the second pair of gauge points are 3.0 mm apart) and the measure difference is 1.1 mm, a determination can be made that the strain/displacement measuring device is not properly calibrated and is off by +10%. Such an adjustment/correction to measurements from a strain/displacement measuring device can be used to isolate load measurements to determine whether load measuring devices are properly calibrated and can eliminate false indications of a correct calibration.

Such calibration checkers can be used with any of a variety of appropriate materials testing systems, such as Disk-shaped Compact Tension (DCT) test machines. For example, DCT test machines have been used to test a variety of materials, such as asphalt. To test a material specimen using a DCT test machine, the material mixture can formed into a specified disk-shaped configuration, gauge points can be attached at either side of a portion of the specimen where displacement will occur when a load is applied to the specimen (e.g., either side of a crack), and a Crack Mouth Opening Displacement (CMOD) Gauge can be attached to the gauge points and measure displacement/strain as a load is applied to the specimen. A calibration checker can be sized and shaped to fit within such a DCT test machine and can be made from an elastic material, such as aluminum, so as to provide for reliable and consistent energy measurements as the elastic materials is stretched by the DCT test machine. Such a calibration checker can be configured to return back to its original shape and be ready for another test after being used by a DCT test machine.

When testing the calibration of a DCT test machine, a calibration checker can be configured with two or more auxiliary gauge points spanning different distances and with a known difference in distance. The calibration of the CMOD gauge can tested by measuring the distances of these auxiliary gauge points and comparing the difference of these measurements to the known difference. Based on this comparison a determination can be made as to whether the CMOD gauge is properly calibrated and, if not, the degree to which the calibration is off (e.g., +10%, −5%). Using such calibration information for the CMOD gauge, an energy measuring test on the calibration checker can be performed to determine whether a load measuring device of the DCT test machine is properly calibrated. Energy measurements taken by the DCT test machine for the calibration checker can be compared with a known energy characteristic for the calibration checker to determine whether the DCT test machine is properly calibrated and within a threshold tolerance.

A variety of additional and different features are described with regard to the figures below.

FIG. 1 is a conceptual diagram of an example system 100 for checking calibrations of a materials testing system. The example system 100 includes a calibration checker 102 and a computer system 104.

The example calibration checker 102 can include a calibration specimen 106 and a plurality of pairs of physical elements that define fixed distances 108a-b. The calibration specimen 106 can be sized and shaped to fit within and to be properly tested by one or more materials testing systems, such as a DCT test machine and a tensile strength testing machine. The calibration specimen 106 can be made of one or more materials that are elastic up to at least a threshold level of force (e.g., elastic up to 4,000 N, 8,000 N) so that the calibration specimen 106 can return to its same shape after a load up to the threshold level of force has been applied to and removed from the calibration specimen 106. The example calibration specimen 106 that is depicted in FIG. 1 is sized and shaped for use with a DCT test machine (and/or other suitable materials testing systems). Other sizes and shapes are also possible.

The calibration specimen 106 can additionally be sized, shaped, and made of material that permit for parity or near parity (within a threshold tolerance) between percentage change in strain/displacement and the percentage change in the load as a load is applied to the calibration specimen 106. For example, the calibration specimen 106 can be configured so that as the force applied to the calibration specimen 106 increases by 10%, the displacement for the calibration specimen 106 increases by or near 10%. Such parity or near parity between the percentage change in the strain/displacement measurements and the percentage change in the load measurements can allow for a greater level of granularity and accuracy with which energy can be measured for the calibration checker 102, which can additionally improve the accuracy of a calibration test performed using the calibration checker 102.

The calibration checker 102 additionally includes two pairs of gauge points 108a-b, which are examples of pairs of physical elements that define fixed distances (other implementations are also possible). The gauge points 108a-b can define fixed and known distances $D_0$ and $D_1$ that can be used to determine whether stain/displacement measuring devices of a materials testing system is properly calibrated, as described below with regard to steps B and C. For example, the difference between the distances $D_0$ and $D_1$ can be a known value $(D_1-D_0)$ and can be compared to measured distance values for the gauge points 108a-b using a strain/displacement measuring device to determine whether the strain/displacement measuring device is properly calibrated.

Although depicted in this implementation as being attached to the calibration specimen 106, the gauge points 108a-b can be attached to one or more separate physical objects, such as a block of material sufficient in size for mounting the gauge points 108a-b. The gauge points 108a-b are one example of pairs of physical elements that define fixed distances—other implementations are also possible. For example, one or more of the pairs of physical elements could be defined by one or more voids in the sidewall of the calibration specimen 106.

The calibration checker 102 can additionally include gauge points 110 (example a pair of physical elements) that define a variable distance span that will change as loads are applied to the calibration specimen 106 by a materials testing system. The gauge points 110 can be sufficient in size and shape to engage one or more strain/displacement measuring devices.

The computer system 104 can be any of a variety of appropriate computing systems to analyze results from tests performed using the calibration checker 102, such as desktop computers, laptop computers, tablet computing devices, mobile computing devices (e.g., smartphones, personal digital assistants (PDAs)), calculators (e.g., electronic computing devices that are programmed to perform, at least, arithmetic operations, such as pocket calculators and graphing calculators), embedded computing systems (e.g., computing systems embedded within a materials testing system), networked computing resources (e.g., cloud-computing resources), computer server systems, or any combination thereof. The computer system 104 is programmed to obtain information regarding the calibration specimen 102 and to use the obtained information to determine whether a materials testing system is properly calibrated based on measurements taken with regard to the calibration checker 102. Such operations can be implemented by the computer system 104 in any of a variety of appropriate manners, such as in software (e.g., program that is loadable into memory and executable by a computer processor), hardware (e.g., application specific integrated circuit (ASICs)), firmware, or any combination thereof. In some implementations, the computer system 104 can be included as part of a materials testing system (e.g., an embedded computer system within the materials testing systems).

Referring to step A (112), information for the calibration checker 102 can be accessed by the computer system 104. Such information can include information that identifies known distances for the gauge points 108a-b (distances $D_0$ and $D_1$) and/or differences between the known distances for the gauge points 108a-b ($D_1-D_0$). Such information can additionally include an energy characteristic for the calibration specimen 106 that indicates a relationship between the strain/displacement of the calibration specimen 106 and the load applied to the calibration specimen 106 to cause the strain/displacement.

The information can be accessed in any of a variety of appropriate ways, such through detecting the information from the calibration checker 102 (e.g., embedded/attached RFID tag containing the information, optical scan of encoded information (e.g., QR code, bar code), optical interpretation of written information (e.g., image capture and text recognition feature)), through interaction with a data source external to the calibration checker 102 (e.g., interaction with a network-accessible database system storing information for particular calibration checkers, reference stored information in the computer system 104 for the calibration checker 102), and/or through manual entry into the computer system 104 (e.g., user can manually input (e.g., text, speech) information printed on the calibration checker 102 into the computer system 104).

For example, in some implementations the calibration checker 102 includes information 114 that can include information for the calibration checker 102 (e.g., energy characteristic, distance for the gauge points 108a-b) and/or can include an identifier that can be used to obtain such information from another source (e.g., network accessible database). The information 114 may be provided in any of a variety of appropriate formats, such as through computer-readable means (e.g., RFID tag, QR code, bar code, text for optical recognition, computer accessible port through which nonvolatile memory attached to/embedded within the specimen 106 can be accessed (e.g., USB-accessible flash memory)) and/or in writing on the calibration specimen 106.

At step B (116), the calibration for a distance measuring device 118 (strain/displacement measuring device) is tested based on the access information for the calibration checker 102. The distance measuring device 118 can be any appropriate type of device to measure strain and/or displacement of the calibration specimen 106 as a load is applied to the calibration specimen 106, such as CMOD gauges, linear variable displacement transducers (LVDT), extensometers, and/or dial indicators. To test the calibration of the distance measuring device 118, measurements of the gauge points 108a-b using the distance measuring device 118 can be taken and received by the computer system 104 and can be compared to the accessed information for the calibration checker 102. For instance, the distance measuring device 118 can produce two distance measurements $MD_0$ and $MD_1$ for the fixed distance spans that are defined by the gauge points 108a-b. The computer system 104 can obtain such measurements (e.g., through electronic signal received from the distance measuring device 118, either directly or indirectly through another device) and can determine a difference between the two distance measurements ($MD_1-MD_0$) and can be compared to the known difference between the fixed distance spans ($D_1-D_0$). These distance differences can be compared to determine whether the distance measuring device 118 is properly calibrated. For instance, if the measured difference value ($MD_1-MD_0$) deviates from the known difference value ($D_1-D_0$) by more than a threshold amount (e.g., more than 1%, more than 3%, more than 5%, more than 8%, more than 10%), then a determination can be made that the distance measuring device 118 is not properly calibrated. In contrast, if the measured difference value ($MD_1-MD_0$) is within a threshold amount of the known difference value ($D_1-D_0$), then the distance measuring device 118 can be determined to be properly calibrated.

The example distance measuring device 118 can be any of a variety of appropriate devices, such as contact measuring devices that measure distances based on physical contact by the contact measuring devices with physical objects that define distance spans (e.g., CMOD gauges, draw wire distance sensors) and/or non-contact measuring devices that measure distances without physically contacting physical objects that define distance spans (e.g., magneto restrictive measuring devices, capacitive measuring devices, laser measuring devices, visual measuring devices). For example, the distance measuring device 118 can be a magneto restrictive transistor that is configured to determine the distance between and/or displacement of two or more magnets, such as neodymium magnets. In such examples, the physical elements that define the fixed distance spans 108a-b and the gauge points 110 can be pairs of magnets for which the magneto restrictive transistor is able to measure a distance between the pairs of magnets (e.g., neodymium magnets) without physically contacting the pairs of magnets.

In another example, the distance measuring device 118 can be a device that uses lasers to measure distance between physical objects without physically touching the objects, such as laser rangefinders that use time of flight to determine distances, laser distance sensors, laser gauging sensors, laser displacement sensors, and/or any combination thereof. In such examples, the physical elements that define the fixed distance spans 108a-b and the gauge points 110 can be configured to properly work with an appropriate laser measuring device, such as by having a flat and/or reflective surface to sufficiently reflect laser pulses or by being configured to properly house one or more sensors.

In a further example, the distance sensor 118 can be a device that uses capacitive sensors (e.g., non-contacting displacement transducers) to measure the distance between physical objects using eddy currents and without physically touching the objects. In such examples, the physical elements that define the fixed distance spans 108a-b and the gauge points 110 can be configured provide changes in impedance that provides a linear electrical signal that is proportional to a distance between a target and a sensor, such as using conductive materials that are ferromagnetic or non-ferromagnetic.

In another example, the distance sensor 118 can be a device that can visually detect displacement between two or more physical objects, such as through the use of a digital camera and one or more image analysis techniques to measure and track changes in distances between visual representations of physical objects. In such examples, the physical elements that define the fixed distance spans 108a-b and the gauge points 110 can be configured to be readily and reliably identified through visual image analysis, such as by being configured with one or more markings (e.g., QR code, other high-contrast encoded markings) and/or with particular shapes and/or sizes.

Other possible configurations and/or combinations of features for the distance sensor 118 and/or the physical elements that define the fixed distance spans 108a-b and the gauge points 110 not explicitly mentioned above are also possible.

As indicated by Step C (120), if the distance measuring device 118 is determined to not be properly calibrated, then a determination can be made as to a correction that should be applied to measurement produced by the distance measuring device 118. For example, the correction can be determined based on a percentage difference between the measured difference value ($MD_1 - MD_0$) and the known difference value ($D_1 - D_0$). For instance, the correction can be:

$$\text{Displacement Correction Factor} = \frac{(MD1 - MD0)}{(D1 - D0)} \quad \text{EQUATION 1}$$

The correction can be applied to measurements that are taken using the distance measuring device 118 when testing the calibration of load measuring devices and/or materials samples. Such a correction can be applied using the following equation:

Corrected Measurement=Correction Factor×Measurement   EQUATION 2

At step D (122), the calibration of a load measuring device 124 of a materials testing system 126 can be tested. The load measuring device 124 can be any of a variety of appropriate devices that are capable of measuring force applied to the calibration specimen 106, such as one or more transducers. The load measuring device 124 can be part of the materials testing system 126, which is configured to exert a stress upon a material specimen to induce a strain/displacement in the specimen that can be measured by the distance measuring device 118. The materials testing system 126 can have any of a variety of different configurations, such as a DCT test machine and/or a tensile strength testing machine. The depicted example materials testing system 126 is a simplified side view of a DCT test machine that includes testing arms 128 that engage the opening in the calibration specimen 106 to exert a load upon the calibration specimen 106, as indicated by the opposed arrows along each of the testing arms 128. As the load is applied to the calibration specimen 108 by the materials testing system 128, the load measuring device 124 measures that the load that is being applied to the calibration specimen 106 and the distance measuring device 118 measures that strain/displacement of the calibration specimen 106 along the variable distance span defined by the gauge points 110.

The calibration of the load measuring device 124 can be tested by measuring the energy applied to the calibration specimen 106 during the test by the materials testing system 126 and comparing that energy measurement to an energy characteristic for the calibration specimen 106. Such an energy measurement can be determined based on the area under a curve plotting the displacement measurements and the load measurements during the test. With a test of the calibration specimen 106 being performed within an elastic region for the specimen 106 (e.g., forces exerted upon the specimen 106 are less than a yield point for the specimen 106), such a curve can be linear. In such situations, the energy can be determined using the following equation:

Energy=½Force×(Correction Factor×Displacement)   EQUATION 3

In situations where a test on a specimen (e.g., a calibration specimen and/or a material specimen) generates a non-linear curve defined by displacement and force measurements, such as when the test is run outside of an elastic region for the specimen and/or when the specimen is made of a viscoelastic material, the energy can be calculated as the area under the curve. As a test progresses, materials testing systems and/or computer systems can analyze the curve that is generated to calculate the area under a resulting curve using any of a variety of appropriate techniques, such as using Riemann sums and/or curve approximation and integration. The energy can be determined based on an area under the curve determination.

The energy measurement can be compared to an energy characteristic for the calibration specimen 106 that indicates a relationship between force and displacement for the calibration specimen 106, such as a ratio of displacement to force to energy for the calibration specimen 106 (e.g., displacement:force:energy). For instance, the following is an example energy characteristic: 2 mm:2,000 N:2.0 J. Such an energy characteristic can be used to determine whether the load measuring device 124 of the materials testing system 126 is properly calibrated. If the measured energy for the calibration specimen 106 is not consistent with the energy characteristic for the calibration specimen 106, then the load measuring device 124 can be determined to be not properly calibrated. For example, using the example energy characteristic above, if the measured energy for the calibration specimen 106 when tested to 2,000 N in the materials testing system 126 is 2.2 J, then a determination can be made that the load measuring device 124 is not properly calibrated based on the measured energy (2.2 J) being different from the known energy characteristic (2.0 J) for the calibration specimen. In contrast, if the measured energy is within a threshold tolerance (e.g., 0.5%, 1%) of the known energy characteristic for the calibration specimen, then the load measuring device 124 can be determined to be properly calibrated.

As indicated at step E (130), a correction factor for the load measuring device 124 can be determined when the load measuring device is not be properly calibrated. The load correction factor can be based on a comparison of the measured load and the actual load, which can be determined by using the energy characteristic for the calibration specimen 106. For example, the following equation can be used to solve for the actual load value:

$$\text{Actual Load} = \frac{\text{Measured Displacement} \times \text{Energy Characteristic Load}}{\text{Energy Characteristic Displacement}} \quad \text{EQUATION 4}$$

The load correction factor can be determined by comparing the actual load with the measured load. For example, the load correction factor can be determined using the following equation:

$$\text{Load Correction Factor} = \frac{\text{Measured Load}}{\text{Actual Load}} \quad \text{EQUATION 5}$$

As indicated by step F (132), the distance and load measuring devices can be verified using the displacement and load correction factors to provide corrected measurement values. For example, after determining correction factors (if any) based on the tests of the calibration specimen 106, an additional test of the calibration specimen 106 can be run using the correction factors to provide corrected measurement values. Using the corrected measurement values, the steps B-E can be performed again to determine whether the correction factors are sufficient to account for calibration errors in the distance measuring device 118 and/or the load measuring device 124 of the materials testing system 126.

The steps A-F can be performed across different materials testing systems using the same calibration checker 102 to uncover any incorrect calibrations that may be resulting in different measurements across the different materials testing systems. For instance, for testing materials that are prone to having a fair amount of variability across different specimens from the same material mixture, such as asphalt, and for tests that cause such specimens to be destroyed after a single use (meaning that a second materials testing system is unable to verify/double-check the results of a first materials testing system for the same material specimen), it can often be difficult to determine whether different test results across different specimens and different testing systems is caused by the inherent variability of the material being tested (e.g., asphalt) or improper calibrations across different machines. By using the disclosed technology with the calibration checker 102, the uncertainty surrounding improper calibrations can be resolved, which can lead to more certainty as to the variability of the material under test.

Additionally, the steps A-F can be performed at regular intervals for the materials testing system 126, such as before every materials test, after a threshold number of materials tests are run (e.g., every 10 tests, every 20 tests, every 50 tests, every 100 tests), on a daily basis, weekly basis, monthly basis, and/or other appropriate intervals. Regular use of the calibration checker 102 and the associated techniques to verify calibration of the materials testing system 124 and its measurement devices 118 and 124 can be used to provide greater reliability and confidence in the materials testing results that are generated by the materials testing system 124.

Figure 2A:
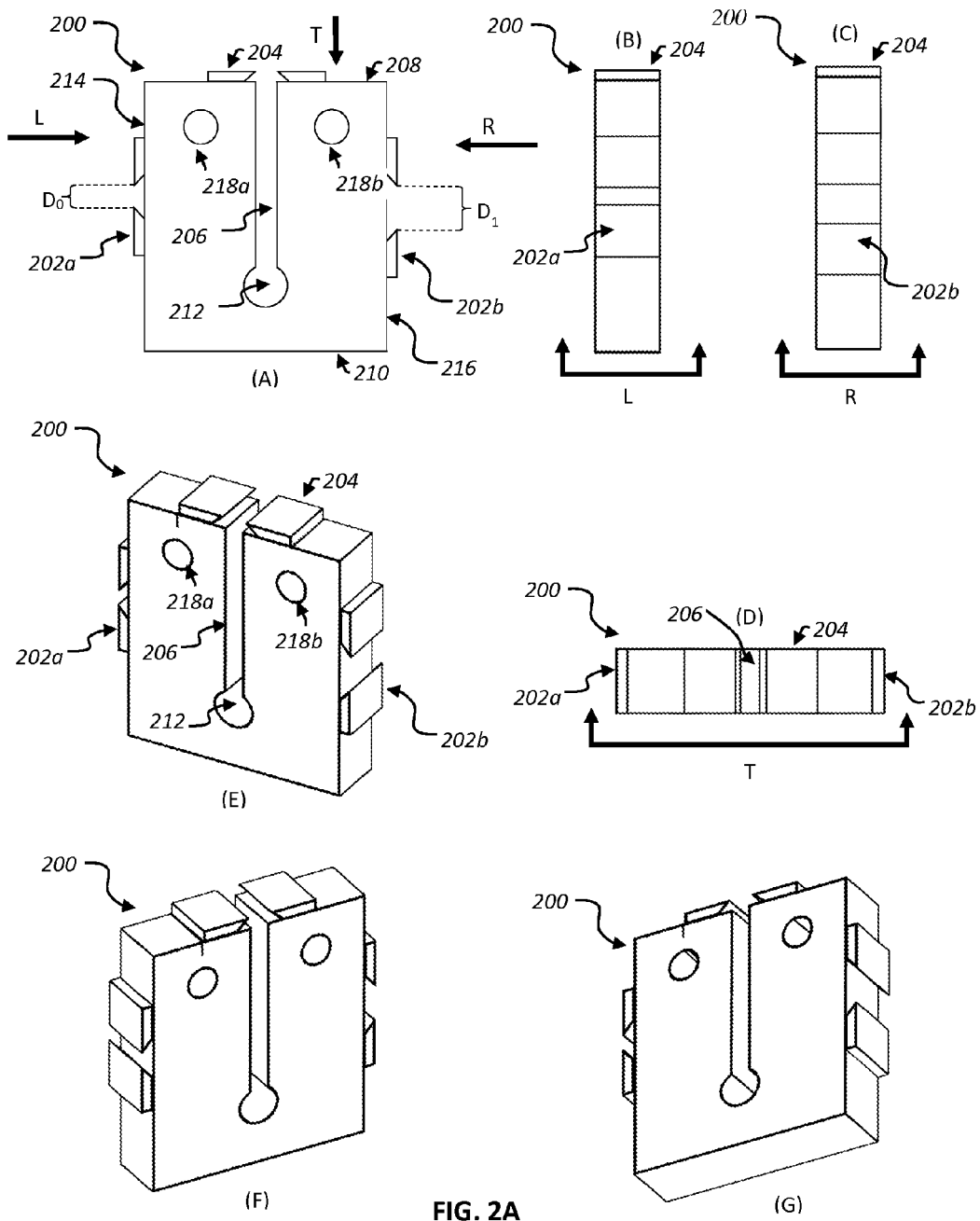
FIGS. 2A-B depict views of example calibration checkers.
Figure 2B:
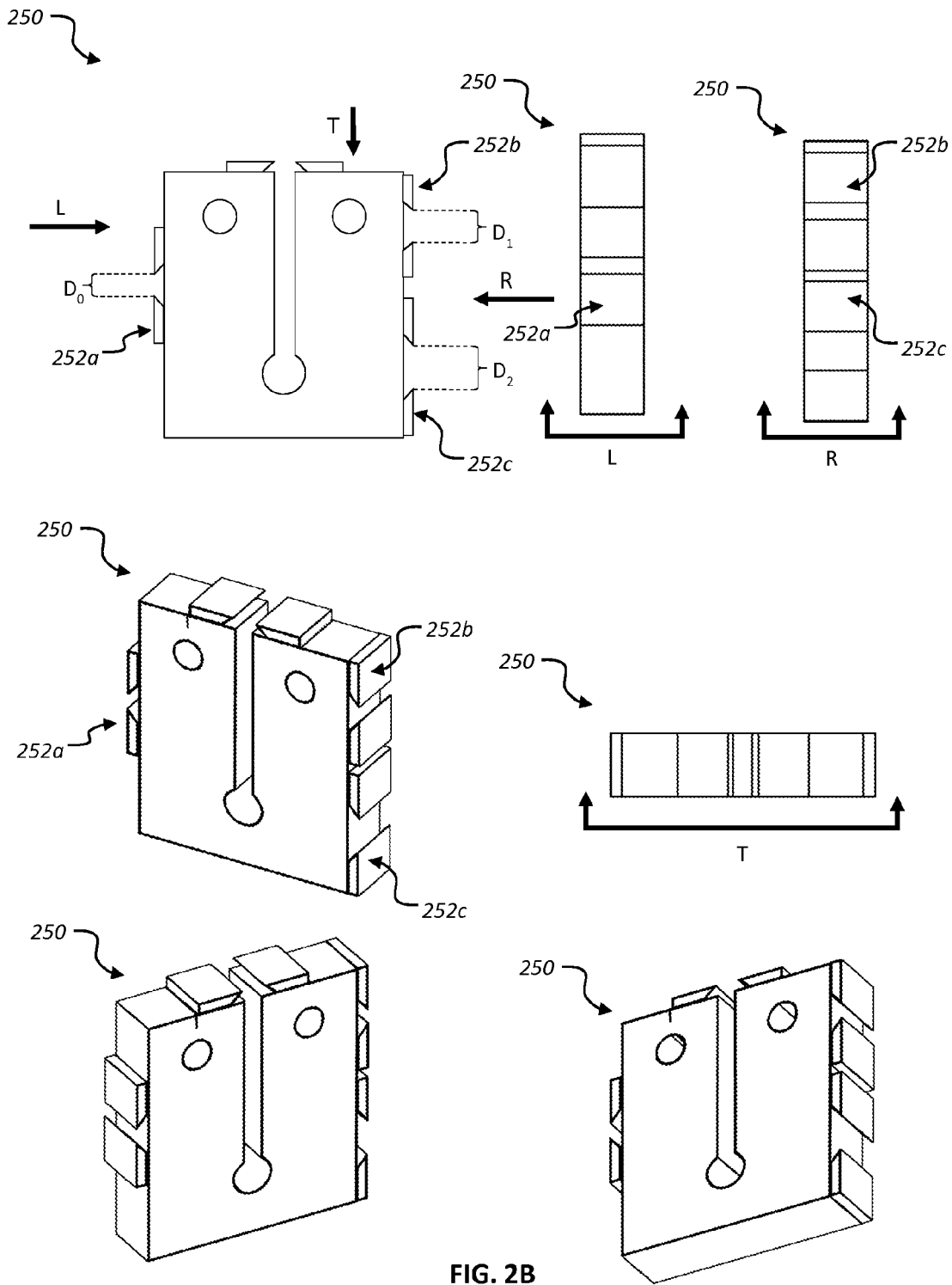

FIGS. 2A-B depict views of example calibration checkers 200 and 250. The calibration checkers 200 and 250 can be similar to the calibration checker 102 that is described above with regard to FIG. 1. The calibration checkers 200 and 250 can be used to verify the calibration of one or more materials testing systems, such as the materials testing system 124 that is described above with regard to FIG. 1.

Referring to FIG. 2A, the example calibration checker 200 includes two pairs of physical elements 202a-b (e.g., gauge points) that define fixed distance spans that can be used to determine whether a distance measuring device is properly calibrated. The calibration checker 200 also includes an additional pair of physical elements 204 that define a variable distance span that changes as loads are applied to the calibration checker 200.

The calibration checker 200 includes a crack 206 that extends perpendicularly from the top surface 208 toward the bottom surface 210 of the calibration checker 200, terminating at an opening 212 in a central region of the calibration checker 200. The crack 206 and the opening 212 can extend through the depth of the calibration checker 200 (from a front surface to a back surface) and can be centered between a first side surface 214 (left surface) and a second side surface 216 (right surface). The opening 212 can be symmetrical in at least a lateral shape (symmetrical across a vertical line bisecting the specimen 200) so as to provide for uniform displacement in lateral directions as loads are applied to the calibration checker 200. The pair of physical elements 204 that provide a variable distance can be position so that the crack is included in the variable distance span.

The example calibration checker 200 that is depicted in FIG. 2A additionally has voids that are defined by openings 218a-b that extend through the front and back surfaces of the calibration checker so as to engage the testing arms of a DCT test machine (or other appropriate materials testing system). By including features to engage a materials testing system while in operational mode (mode during which the materials testing system is equipped to test materials specimens, such as when a materials testing system is configured with specimen grips that hold and transmit loads upon the materials specimens and is using one or more testing programs that cause tests to be performed on and measurements to be obtained for materials specimens), such as the openings 218a-b, the calibration checker 200 can be used to ensure that a materials testing system is properly calibrated while running in operational mode instead of having to assume that no errors were introduced during the conversion from calibration to operational mode. Other configurations are also possible to engage different types of materials testing systems while in operation modes.

The calibration checker 200 can be made of any of a variety of appropriate materials that can be subjected to loads up to a threshold level while still within an elastic region of the material, as indicated by Young's Modulus. An elastic region is a range of loads that is less than a yield point for the material and that, for forces applied within this range, the material returns to its same or similar shape and/or position after the forces have been removed from the material. For example, the calibration checker 200 can be made of materials that have an elastic region that extends up to a threshold level of force, such as 4,000 N, 8,000 N, and/or 20,000 N. Examples of such materials include metals and metal alloys, such as aluminum and aluminum alloys. Additionally, the material should have at least a threshold elasticity so that there is measurable displacement of the calibration checker 200 without needing excessive levels of force to be applied to the calibration checker 200.

In FIG. 2A, view (A) is a front view of the calibration checker 200. A back view is not provided in this figure but would be substantially similar to the front view. View (B) is a view of the first side 214 of the calibration checker. As indicated by the first side view 214, the physical elements 202a and 204 are depicted as extending along the entire depth of the calibration checker 200. The physical elements 202a and 204, as well as other physical elements defining fixed or variable distance spans, may alternatively extend less than the entire depth or greater than the depth of the calibration checker 200. View (C) is a view of the second side 216 of the calibration checker 200 and view (D) is a top view of the calibration checker 200. Views (E-G) are perspective views of the calibration checker 200.

Referring to FIG. 2B, the calibration checker 250 is the same as the calibration checker 200 with the only difference being the use of three pairs of physical elements 252a-c that define three fixed distance spans instead of the two with the calibration checker 200. As discussed above, with two fixed distance spans the difference between the measured distances of these two spans can be compared to a known difference value to determine whether the distance measuring device is properly calibrated. However, when more than two fixed distance spans are defined the number of points of comparison between the measured difference values and the known difference values increases, which can improve the accuracy and granularity for testing the calibration of a distance measuring device. For instance, the following equation provides the number of difference values that can be used as points of comparison based on the number of fixed distance spans (n):

$$\text{Number of Comparisons} = \sum_{1}^{(n-1)} x \qquad \text{EQUATION 6}$$

For instance, when there are two fixed distance spans, as with the calibration checker 200, there is only one point of comparison between the difference of the measured distances for spans 202a and 202b and the known difference in distance between $D_0$ and $D_1$. In contrast, with the calibration checker 250, there are three points of comparison: (1) comparison between (i) measured difference of fixed distance span 252a and 252b and (ii) known difference in distance between $D_0$ and $D_1$; (2) comparison between (i) measured difference of fixed distance span 252a and 252c and (ii) known difference in distance between $D_0$ and $D_2$; (3) comparison between (i) measured difference of fixed distance span 252b and 252c and (ii) known difference in distance between $D_1$ and $D_2$. Accordingly, by increasing the number of fixed distance spans, the number of difference values that can be used to determine the accuracy of the calibration can be increased.

Instead of comparing distance measurements and known distances for the fixed distance spans, differences between distance measurements can be used to avoid a variety of potential sources of error. For example, whether a distance measuring device accurately measures a particular distance correctly may not matter, but instead the displacement (change in distance) is what is used to generate energy measurements and for determining whether a materials testing system is properly calibrated. It may not matter whether a first fixed distance span of 2.0 mm is measured as 2.1 mm and a second fixed distance span of 3.0 mm is measured as 3.1 mm, so long as the difference between two fixed distance spans is consistent with the known difference in distances, which in this example (measured difference of 1.0 mm (3.1 mm–2.1 mm) is consistent with known difference of 1.0 mm) is the case. By focusing on whether a distance measuring device is accurately measuring displacement alone, errors introduced through incorrectly calibrated measurements that do not affect displacement readings can be avoided. In another example, physical elements (e.g., guide points) that define fixed distance spans may wear down over time and, as a result, the raw fixed distance may change over time which would introduce errors if distance measurements alone were used. By consistently measuring distance differences, physical elements are likely to have similar wear patterns which means that the difference between the fixed distance spans is likely to remain constant, even if the distances themselves change slightly over time.

The pairs of physical elements 252a-c can have any of a variety of appropriate configurations to provide for accurate measurements by appropriate distance measuring devices, such as contact distance measuring devices and/or non-contact distance measuring devices, as discussed above with regard to FIG. 1.

In some implementations, distance measurements alone may also be used to determine whether a distance measuring device is properly calibrated.

Figure 3:
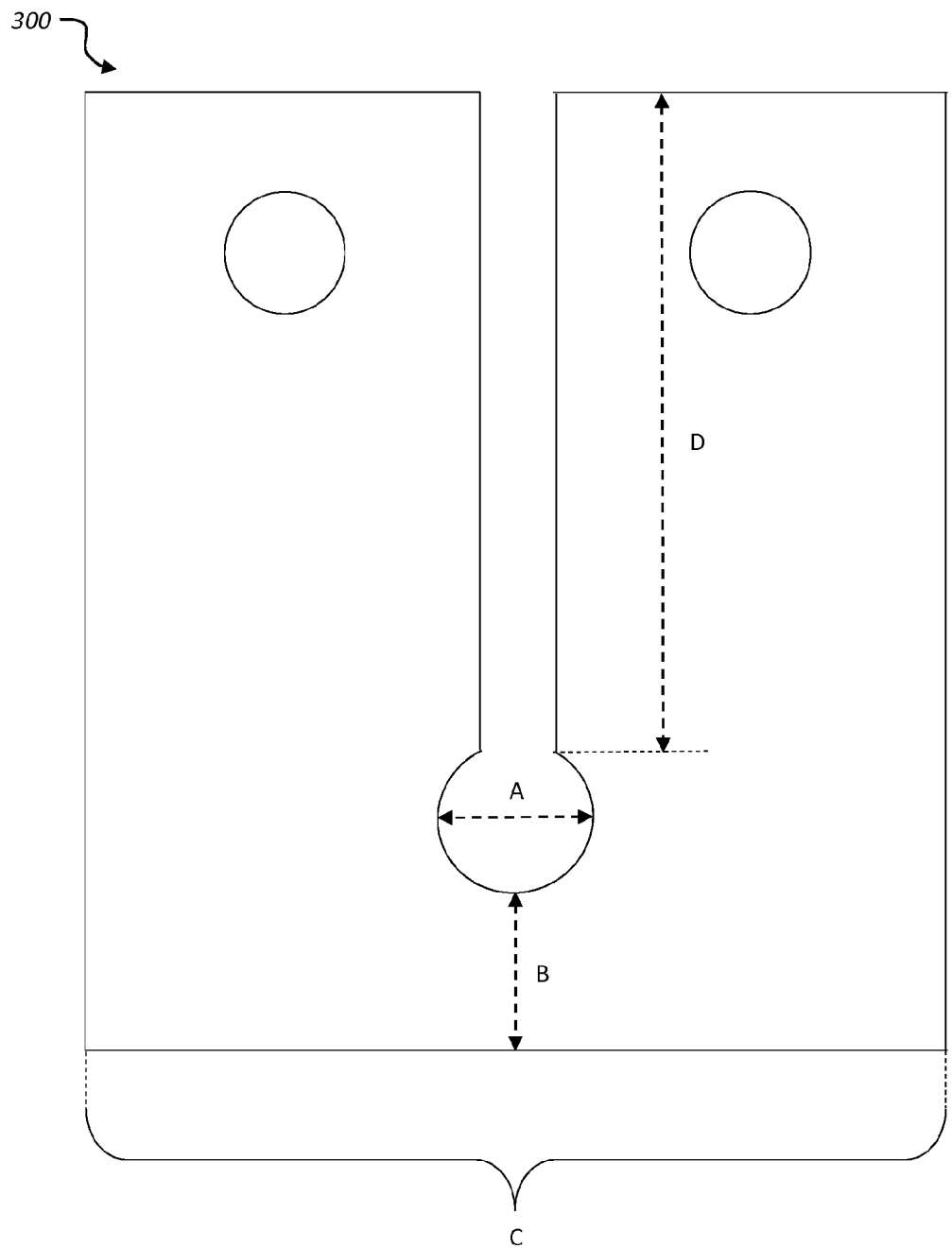
FIG. 3 depicts a front view of an example calibration specimen.

FIG. 3 depicts a front view of an example calibration specimen 300. The example calibration specimen 300 can be similar to the calibration specimens described above with regard to the calibration checkers 102, 200, and 250. The calibration specimen 300 is sized and shaped for use with particular types of materials testing systems, such as a DCT testing machine and/or other testing systems that use similar dimensioned specimens.

The calibration specimen 300 has four dimensions A-D that allow for the calibration specimen 300 to be particularly advantageous for determining whether a materials testing system is properly calibrated. In particular, the dimensions A-D can be selected so that there is at least a threshold degree of parity between a percentage change in displacement and a percent change in load when loads are applied to the calibration specimen 300 in a materials testing system. Such parity or near parity can allow for a greater level of granularity and accuracy for determining whether a materials testing system is properly calibrated.

To generate the calibration specimen 300 to have such properties, the dimensions A-D were experimented with and tested to find one or more optimal dimension sets. The dimension A for the calibration specimen 300 is the diameter of the opening (hole) that is located at the end of the crack extending from the top surface toward the bottom surface of the specimen 300. The opening can be bore through the depth of the specimen 300 and can extend from the front surface of the specimen 300 to the back surface of the specimen 300. Increasing the diameter of the opening (dimension A) can cause the stress to decrease and the deflection to increase. The dimension B is the distance from the bottom edge of the opening (hole) to the bottom surface of the specimen 300. Decreasing the distance to the bottom surface (dimension B) can cause the stress on the specimen 300 to increase and the deflection to increase. The dimension C is the width of the calibration specimen 300. Increasing the width (dimension C) causes the stress on the specimen 300 to increases and the deflection to decrease. And the dimension D is the length of the arms that extend from the base of the specimen 300 along the length of and on either side of the crack. Adjustments to the arm length (dimension D) acts as a multiplier of the deflection of the specimen 300.

Various configurations of such dimensions were tested, some of which are summarized in TABLE 1 below. Calculations were performed using finite element modeling using an aluminum (or similar) material that has an elastic region that extends up to or near 20,000 psi before reaching its yield point. An example of such a material is aluminum 2024. Other suitable materials may also be used.

In order for the calibration specimen 300 to properly fit and work within a DCT test machine in its operational mode, some restrictions/minimum requirements were placed upon the sizing and configuration of the calibration specimen 300. For example, chambers within which DCT specimens are tested by a DCT test machine are limited in size. Accordingly, the bottom distance (dimension B) is limited by a bottom portion of the test chamber and the arm length (dimension D) is limited by a top portion of the test chamber. For example, with a diameter of 0.75" (dimension A), the combination of the bottom distance (dimension B) and the arm length (dimension D) may not exceed 5.35" (or a similar dimension) in order to permit the specimen 300 to function properly under test by a DCT test machine. In another example, the width may not be any smaller than 3" (or a similar dimension) in order to provide sufficient material along the arms between the holes to which the testing arms of a DCT checker attach.

Table 1 below provides four different configurations of the dimensions A-D and the corresponding stress and deflection measurements modeled through the use of finite element modeling. The baseline configuration results in a stress of 19,150 psi and a deflection of 0.0318". Making the bottom distance smaller (dimension B) by 0.355" (or by 32%), the resulting stress is 58,444 psi and the deflection is 0.0964"—which is well outside of the elastic region for the modeled aluminum material (elastic region extends to around 20,000 psi). Making the diameter of the opening smaller (dimension A) by 0.25" causes the stress to decrease from the baseline configuration to 18,700 psi and for the deflection to decrease to 0.0264". Making the specimen 300 wider (dimension C) by 0.5" causes the stress to increase to 19,750 psi and the deflection to decrease to 0.024".

Figure 4A:
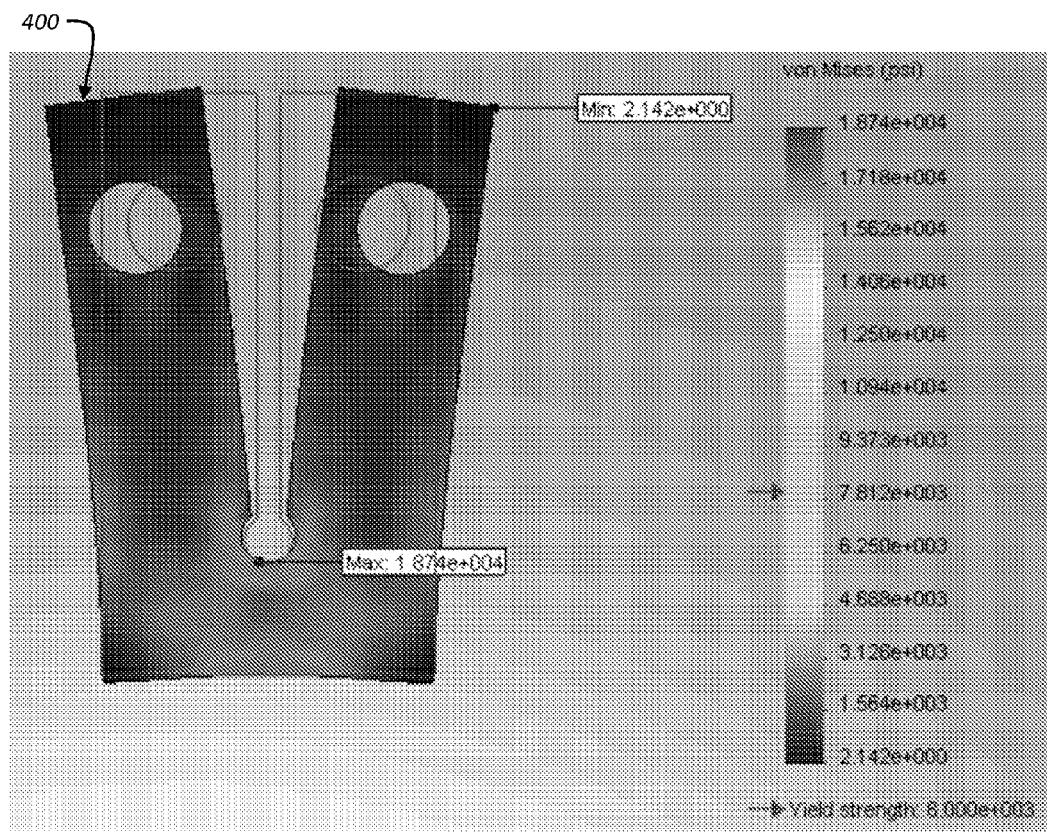
FIGS. 4A-B depict computer models of the strain and displacement on a calibration specimen in response to application of a load.
Figure 4B:
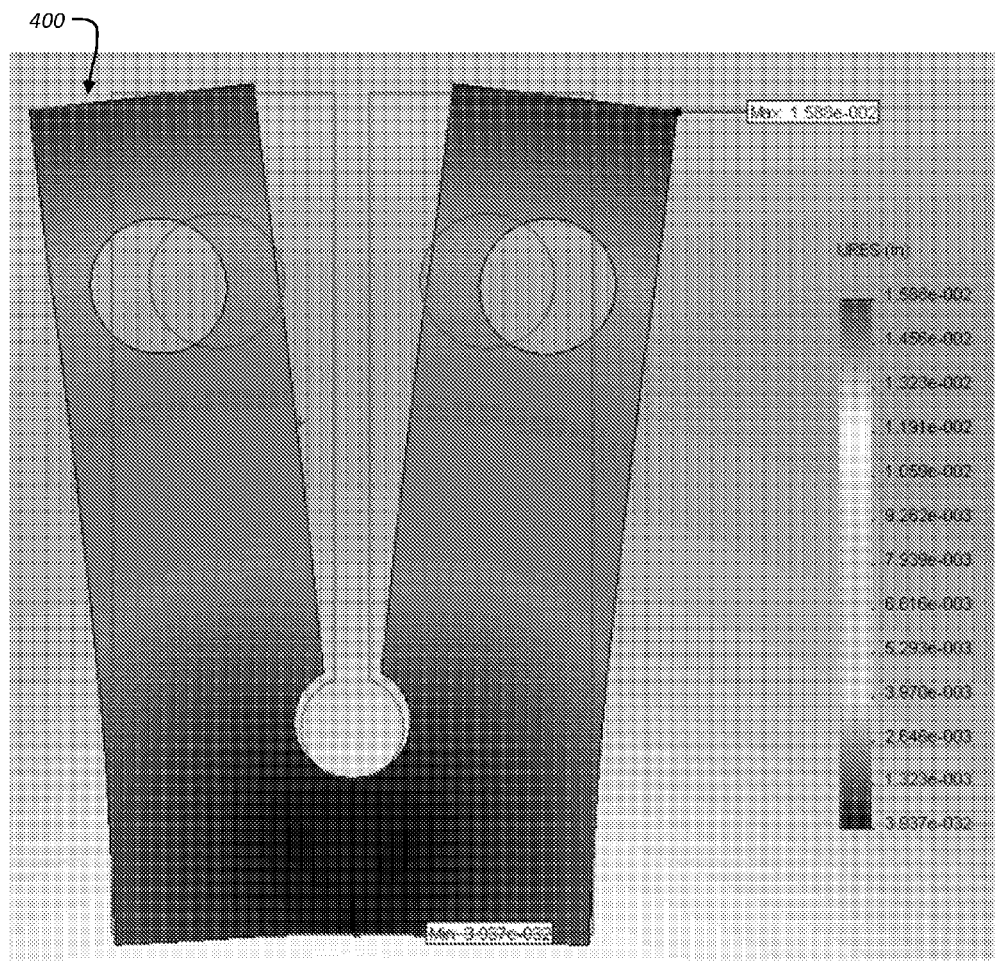

FIGS. 4A-B depict computer models of the strain and displacement on a calibration specimen 400 in response to application of a load. The computer models can be used to determine appropriate dimensions for a calibration specimen, as described above with regard to FIG. 3. The computer models can be generated in any of a variety of appropriate ways, such as finite element modeling.

The computer model presented in FIG. 4A depicts the strain at various locations of the calibration specimen 400 in response to application of a load. As indicated by the "min" and "max" designators, the minimum strain is 2.142 psi at the top right corner of the specimen 400 and the maximum strain is 18,740 psi at the bottom of the opening at the base of the calibration specimen 400.

The computer model presented in FIG. 4B depicts the displacement at various locations of the calibration specimen 400 in response to application of a load. As indicated by the "min" and "max" designators, the minimum displacement is $3.937e^{-32}$ inches at the center of the bottom surface of the specimen 400, and the maximum displacement is 0.01588 inches in the upper right hand corner of the specimen 400.

Figure 5:
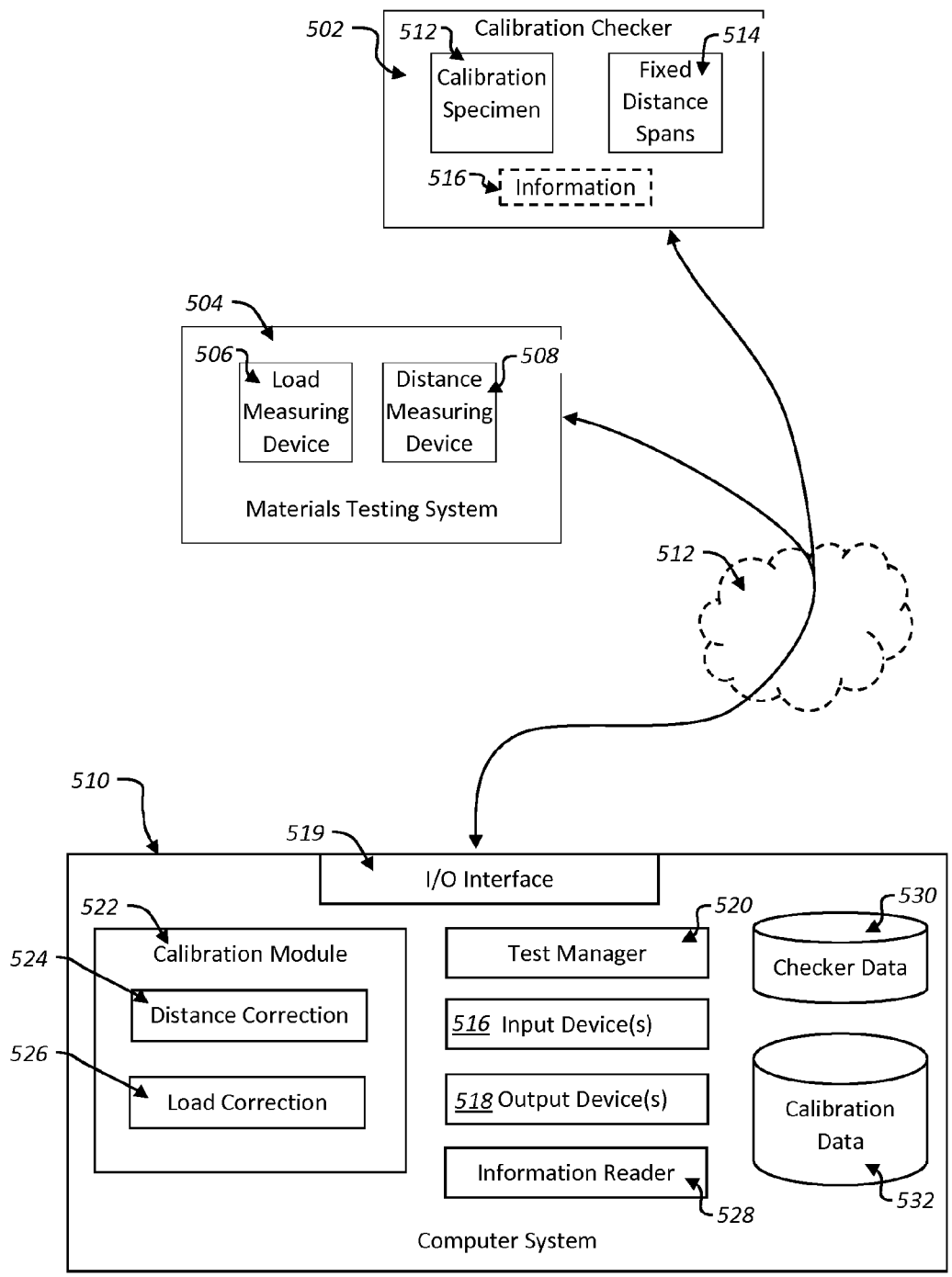
FIG. 5 depicts an example system for testing calibrations of a materials testing system.

FIG. 5 depicts an example system 500 for testing calibrations of a materials testing system. The example system 500 includes a calibration checker 502, a materials testing system 504 with a load measuring device 506 and a distance measuring device 508, and a computer system 510. The system 500 can be similar to the system 100 described above with regard to FIG. 1. The materials testing system 504 can be similar to the materials testing systems described above, such as the materials testing system 126 described above with regard to FIG. 1.

The calibration checker 502 can be tested by the materials testing system 504 and the measurements from such a test can be used to determine whether the measuring devices 506 and

TABLE 1

|  | Baseline | Smaller Bottom Distance (Dimension B) | Smaller Diameter (Dimension A) | Wider (Dimension C) |
|---|---|---|---|---|
| Dimension A (inches) | 0.75 | 0.75 | 0.5 | 0.5 |
| Dimension B (inches) | 1.105 | 0.75 | 1.105 | 1.105 |
| Dimension C (inches) | 3.5 | 3.5 | 3.5 | 4 |
| Dimension D (inches) | 4.245 | 4.245 | 4.245 | 4.245 |
| STRESS (psi) | 19,150 | 58,444 | 18,700 | 19,750 |
| DEFLECTION (inches) | 0.0318 | 0.0964 | 0.0264 | 0.024 |

The information provide in Table 1 is from analysis done with application of a load of 3,2000 N in a DCT test machine. Tests in a DCT test machine of calibration specimens can be performed in any of a variety of appropriate manners, which can be based on one or more materials for which the calibration of the DCT test machine is being evaluated. For example, typical asphalt tests in a DCT test machine are run out to around 4,000 N and result in a displacement of around 2.0 mm, at or near which a yield point for the specimen is reached and the specimen is destroyed. The calibration specimen 300 run through a DCT test machine can be run out a portion (e.g., quarter, one-third, half, two-thirds, three-quarters) of the total force and displacement of an asphalt specimen in order to ensure that the calibration specimen 300 does not accidental run into its yield point. For example, tests on the calibration specimen 300 can be run out to 2,000 N and with a displacement of 1.0 mm to provide a margin of safety for the calibration specimen 300 in case something accidently goes wrong with the test.

Additional configurations not include in Table 1 are also possible.

508 of the materials testing system 504 are properly calibrated. The calibration checker 502 can include a calibration specimen 512 and a plurality of physical elements that 514 that define fixed distance spans. The distance measuring device 508 can be any of a variety of appropriate distance measuring device, such as contact distance measuring devices and/or non-contact distance measuring devices, and the plurality of physical elements 514 can have any of a variety of appropriate configurations to provide for accurate measurements by the distance measuring device 508, as discussed above with regard to FIG. 1.

The calibration checker 502 can, in some implementations, include information 516 that, directly or indirectly, provides an energy characteristic for the calibration specimen 512, known distance and/or known distance difference information for the fixed distance spans 514, and other appropriate information. As discussed above with regard to the information 114, the information 516 may be provided by a mechanism that is part of and/or affixed to the calibration checker 502, such as an RFID tag, a QR code, and/or a barcode. The information 516 may either provide details regarding the calibration checker 502 or may identify the calibration checker 502 (e.g., unique identifier for the calibration checker 502, such as a serial number) and/or a source from which details regarding the calibration checker 502 can be obtained (e.g., URL of an internet accessible resource from which details for the calibration checker 502 can be obtained using a unique identifier for the calibration checker 502). The calibration checker 502 can be similar to the calibration checkers described above, such as the calibration checkers 102, 200, 250, 300, and/or 400 that are described above with regard to FIGS. 1-4.

The computer system 510 can include one or more appropriate computing devices, such as desktop computers, laptop computers, portable computing devices (e.g., smartphones, PDAs), calculators, tablet computing devices, embedded computing devices, computer servers, cloud-computing systems, or any combination thereof. The computer system 510 can obtain information from the calibration checker 502 and the materials testing system 504, in some implementations, using one or more communication networks 512. The communication networks 512 can include local area networks (LANs), wide area networks (WANs), virtual private networks (VPNs), wireless networks (e.g., Wi-Fi networks, Wi-Di network connections, 3G/4G mobile data networks), short-range wireless connections (e.g., Bluetooth network connections, near-field communication networks), the internet, or any combination thereof. The information from the calibration checker 502 and/or the materials testing system 504 can be received by the computer system 510 at an input/output (I/O) interface 519, which can include one or more interfaces through which the computer system 502 can communicate with other devices, such as wireless communication chips (e.g., Wi-Fi chips, 3G/4G chips), Ethernet cards and ports, USB ports, display ports, or any combination thereof.

The computer system 510 can further include input devices 516 and output devices 518 through which user input can be received and output can be provided to users by the computer system. The input devices 516 can include any of a variety of appropriate input devices, such as keyboards, pointing devices (e.g., mouse, trackball), touch interfaces (e.g., touchscreens, touchpads), microphones, cameras, motion and presence sensing devices (e.g., MICROSOFT KINECT device and interface), or any combination thereof. The output devices 518 can include any of a variety of appropriate output devices, such as a computer display, speakers, printers, and/or projectors.

The computer system 510 can include a test manager 520 and a calibration module 522. The test manager 520 can be programmed to manage one or more tests that are performed by the materials testing system 504, including calibration tests that are performed using the calibration checker 502. The test manager 520 can communicate with the materials testing system 504 to control operation of the materials testing system 504 and to receive measurements from the load and distance measuring devices 506 and 508 during the tests. The calibration module 522 is programmed to determine whether the materials testing system 504 and its measuring devices 506, 508 are properly calibrated based on tests that are run using the calibration checker 502, as described above. The calibration module 522 includes a distance correction module 524 that is programmed to determine, if appropriate, a correction to distance measurements that are generated by the distance measuring device 508. The calibration module 522 also includes a load correction module 526 that is programmed to determine, if appropriate, a correction to load measurement that are generated by the load measuring device 506. The test manager 520 and the calibration module 522 can be implemented in any of a variety of appropriate ways, such as through software, firmware, hardware, or any combination thereof.

The computer system 510 can additionally include on or more information readers 528 which are devices to read/access the information 516 that is provided as part of the calibration checker 502. For example, the information reader 528 can be a device to read RFID tags, a device to optically process QR codes, a device to scan and read barcodes, and/or a device to optically read printed text.

The computer system 510 can additionally include a checker data repository 530 to store information for one or more calibration checkers 502, such as energy characteristics and distance information, and can include a calibration data repository 532 to store information regarding calibration tests that are performed (e.g., timestamp of the test, results of the test, identification of the materials testing system under test, identification of the calibration checker that was used during the test, specific results that were produced). The repositories 530 and 532 can be any of a variety of appropriate data storage systems, such as databases, flat file systems, comma separate data files, and/or hash-based storage systems. The data repositories 530 and 532 may local to and/or remote from one or more computers that are part of the computer system 510 and, in some implementations, may be internet-accessible storage systems.

In some implementations, the computer system 510 can be included as part of the materials testing system 504. For example, the computer system 510 can be one or more computing devices that are embedded within the materials testing system 504.

Figure 6:
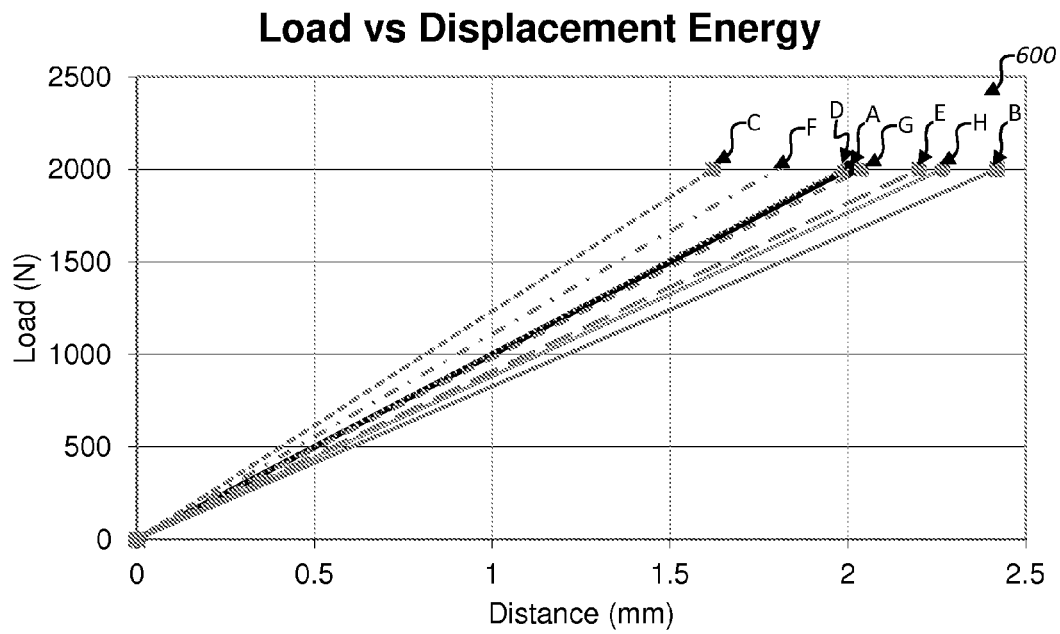
FIG. 6 depicts graphs that plot measurements from a materials testing system with various error scenarios.
Figure 6:
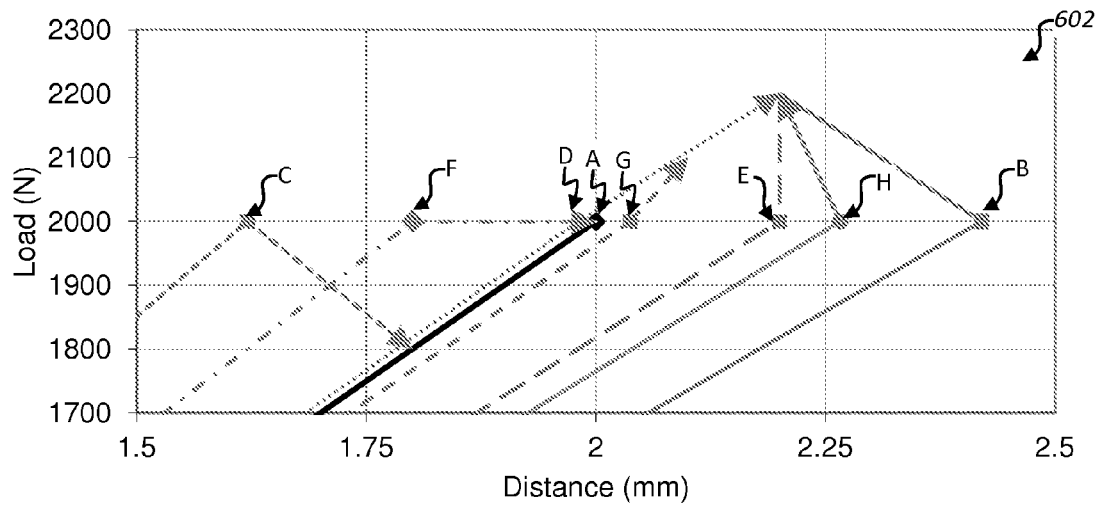

FIG. 6 includes graphs 600 and 602 that plot measurements from a materials testing system with various error scenarios.

As detailed in Table 3 below, plots A-H are presented on graphs 600 and 602. There are nine basic categories into which these plots fit depending on whether there is a positive error, a negative error, or no error with regard to distance and load measuring devices that are part of a materials testing system that is under analysis, as indicated in Table 2 below. The disclosed calibration testing techniques in this document are able to distinguish between each of these nine categories of error situations, even though some categories may have offsetting errors that provide the appearance of being within another category (e.g., a positive distance error of similar magnitude to a negative load error may have the appearance of being in the no load error and no distance error category). For instance, Plot A in graphs 600 and 602 is has no errors, yet Plots D and G (which both have load and displacement errors) are very similar to Plot A in that their reported load and displacement is similar to Plot A. Error conditions such as Plots D and G can provide false indications of calibration. However, by determining whether a distance measuring device is properly calibrated and, if it is not properly calibrated, using a calibration factor for the distance measuring device an accurate determination of whether a load measuring device is properly calibrated can be made.

TABLE 2

|  | Positive Load Error | No Load Error | Negative Load Error |
|---|---|---|---|
| Positive Distance Error | Plots B and H | | |
| No Distance Error | Plot E | Plot A | |
| Negative Distance Error | Plots D and G | Plot F | Plot C |

Table 3 below includes details regarding the Plots A-H that are presented on the graphs 600 and 602. Each of the Plots A-H is for a test in a materials testing system with varying degrees of load and distance measuring error, where the each of tests are run out to a measured load of 2,000 N. In particular, Table 3 indicates the load error (error in the load measuring device), the distance error (error in the distance measuring device), the measured change in load (N) for the test, the actual change in load (N) during the test, the measured change in distance (mm) during the test, the actual change in distance (mm) during the test, the measured energy (measured load× measured distance/2) for the test, the actual energy (actual load×actual distance/2) for the test, the corrected energy (measured load×((1−distance error)×measured distance)/2) when the measured distance is corrected for the distance error (which can be identified using measured differences between fixed distance spans, as described above), the measured percentage (measured energy/actual energy) for the test, the corrected percentage (corrected energy/actual energy) for the test when correcting for the distance error, and the comparison (corrected energy/2,000−energy characteristic from Plot A) between the corrected energy and the energy characteristic for the calibration checker being used for the tests, which is presented in Plot A.

error is 5%), and the results for Plot H indicate that the load measuring device is measuring high by 9.9% (actual load error is 10%).

The graph 600 plots the measured load and distance values. The graph 602 plots the measured load and distance values, and includes arrows from the end value to the actual load and distance values during the test.

Figure 7:
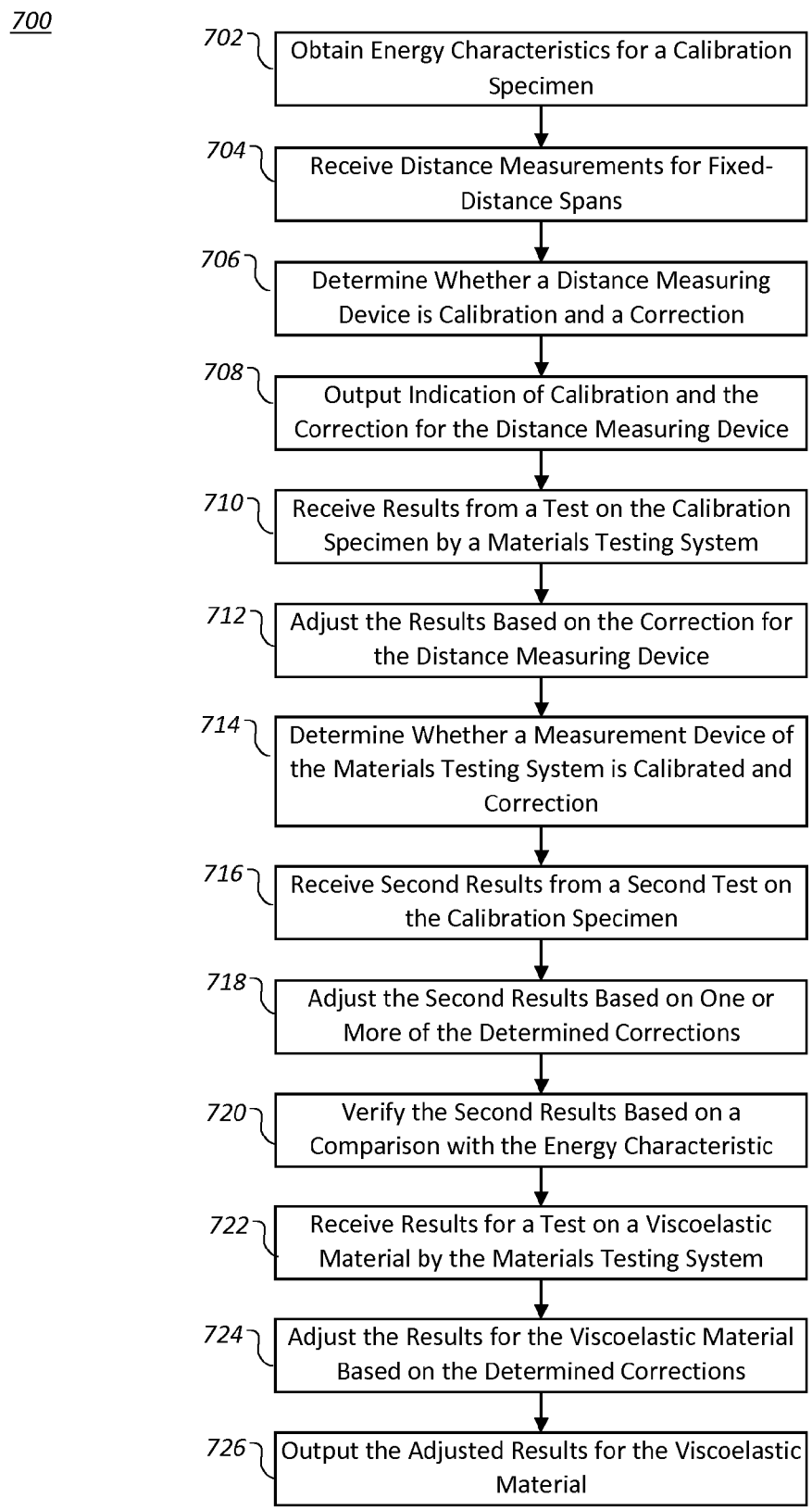
FIG. 7 is a flowchart of an example technique for determining whether a materials testing system and its measuring devices are properly calibrated.

FIG. 7 is a flowchart of an example technique 700 for determining whether a materials testing system and its measuring devices are properly calibrated. The example technique 700 can be performed by any of a variety of appropriate computing devices, such as the computer system 104 described above with regard to FIG. 1 and/or the computer system 510 described above with regard to FIG. 5.

An energy characteristic for a calibration specimen can be obtained (702). For example, the information reader 528 of the computer system 510 can access the information 516 from the calibration checker 502. In instances where the information 516 contains an identifier for the calibration checker 502, the computer system 510 can use the identifier to access the energy characteristic information from either a local source or a remote source, such as a remote database system accessible over one or more networks. Access to such energy characteristic information may be restricted and may require login or

TABLE 3

|  | A | B | C | D | E | F | G | H |
|---|---|---|---|---|---|---|---|---|
| Load Error | 0.0 | 0.1 | −0.1 | 0.1 | 0.1 | 0.0 | 0.05 | 0.1 |
| Distance Error | 0.0 | 0.1 | −0.1 | −0.1 | 0.0 | −0.1 | −0.03 | 0.03 |
| Measured Load | 2000 | 2000 | 2000 | 2000 | 2000 | 2000 | 2000 | 2000 |
| Actual Load | 2000 | 2200 | 1800 | 2200 | 2200 | 2000 | 2100 | 2200 |
| Measured Distance | 2.0 | 2.2 | 1.62 | 1.98 | 2.2 | 1.8 | 2.037 | 2.27 |
| Actual Distance | 2.0 | 2.42 | 1.8 | 2.2 | 2.2 | 2.0 | 2.1 | 2.2 |
| Measured Energy | 2000 | 2420 | 1620 | 1980 | 2200 | 1800 | 2037 | 2266 |
| Actual Energy | 2000 | 2420 | 1620 | 2420 | 2420 | 2000 | 2205 | 2420 |
| Corrected Energy | 2000 | 2178 | 1782 | 2178 | 2200 | 1980 | 2098 | 2198 |
| Measured Percentage | 100% | 100% | 100% | 81.8% | 90.9% | 90% | 92.4% | 93.6% |
| Corrected Percentage | 100% | 90% | 110% | 90% | 90.9% | 99% | 95.1% | 90.8% |
| Energy Characteristic Comparison | N/A | 108.9% | 89.1% | 108.9% | 110% | 99% | 104.9% | 109.9% |

When performing tests, the actual energy is not a known value. Instead, the known value is the energy characteristic for the calibration specimen that is being used for the tests, which is provided in Plot A. The comparison with the energy characteristic for the calibration specimen under test can provide an accurate indication of whether a load measuring device is properly calibrated. For example, the results for Plot B indicate that the load measuring device is measuring high by 8.9% (actual load error is 10%), the results for Plot C indicate that the load measuring device is measuring low by 10.9% (actual load error is −10%), the results for Plot D indicate that the load measuring device is measuring high by 8.9% (actual load error is 10%), the results for Plot E indicate that the load measuring device is measuring high by 10% (actual load error is 10%), the results for Plot F indicate that the load measuring device is near accurate and is off by 1% (no actual load error), the results for Plot G indicate that the load measuring device is measuring high by 4.9% (actual load other types authentication to obtain access to the energy characteristic information. For example, the energy characteristic information may maintained on a remote computer system that provides access to the energy characteristic information on a paid basis (e.g., subscription, pay for use, fixed sum payment). In such situations, the energy characteristic information may be maintained on the computer system 510 in a restricted manner such that a user would not be able to duplicate or otherwise access the energy characteristic information improperly. Various techniques could be used to accomplish such restrictions, like encryption and data fragmentation.

Distance measurements for fixed-distance spans that are defined by physical elements can be received (704). For example, the computer system 510 can receive distance measurements for the fixed-distance spans 514 from the distance measuring device 508, possibly over the network 512. A determination can be made as to whether the distance measuring device is properly calibrated and, if appropriate, a correction for measurements from the distance measuring device can be determined (706). For example, the distance correction module 524 of the calibration module 522 can determine whether the distance measuring device 508 is properly calibrated and, if appropriate, can determine one or more corrections for the device 508. An indication of the calibration and the correction for the distance measuring device can be output (708). For instance, the computer system 510 can use the output device 518 to output the indication of calibration (e.g., "distance measuring device is properly calibrated") and any corrections. In another example, the computer system 510 can log the indication of calibration and the correction in the calibration data repository 532.

Results from a test on the calibration specimen by a materials testing system can be received (710). For example, the computer system 510 can receive results, such as load measurements, distance measurements, and/or energy measurements, from the materials testing system 504 and its measuring devices 506 and 508. The received results can be adjusted based on the determined correction for the distance measuring device (712). For example, the distance correction module 524 can adjust the distance measurements based on the correction factor that was determined for the distance measuring device 508. A determination can be made as to whether a measurement device of the materials testing system is properly calibrated and, if appropriate, one or more corrections to apply to the measurement device (714). For example, the calibration module 522 can use the adjusted measurements, including a corrected energy measurement, and the energy characteristic for the calibration specimen 512 to determine whether materials testing system 504 and its measuring devices 506 and/or 508 are properly calibrated. For instance, the load correction module 526 can determine whether the load measuring device 506 is properly calibrated based on a comparison of the energy characteristic for the calibration specimen 512 and the corrected test results for the specimen 512, such as a corrected energy measurement. Such a determination regarding calibration and a correction factor for the measurement device of the materials testing system can be output by the computer system 510, such as using the output device 518 and/or the calibration data repository 532.

Second results from a second test on the calibration specimen can be received (716) and can be adjusted based on the determined one or more corrections (718). For example, after determining whether the materials testing system 504 is properly calibrated and correction factors, if appropriate, for the distance measuring device 508 and the load measuring device 506, a second test on the calibration specimen 512 by the materials testing system 504 may be run to verify the correction factors and calibration. The results from such a second test can be received at the computer system 510 and can be adjusted by the calibration module 522 according to the correction factors previously determined during the first test. The adjusted second results can be verified based on a comparison with the energy characteristic (720). For example, the calibration module 522 can compare the corrected measured energy from the second test with the energy characteristic for the calibration specimen 512 to verify the calibration and/or correction factors for the materials testing system 504. The results of such a second test can be recorded in the calibration data repository 532.

Results from a test run by the materials testing system on a viscoelastic material can be received (722), can be adjusted based on the previously determined corrections for the materials testing system (724), and can be output (726). For example, a specimen made of a viscoelastic material, such as asphalt, can be tested by the materials testing system following the calibration check (steps 702-720) and the results from the test can be corrected and output according to the determined correction factors for the load measuring device 506 and/or the distance measuring device 508.

Figure 8:
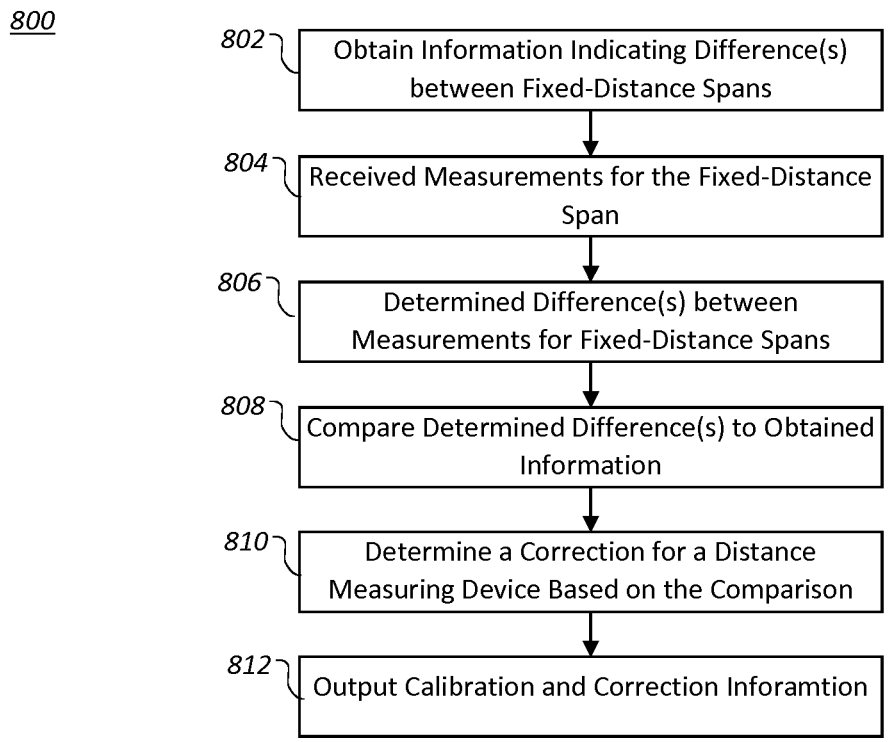
FIG. 8 is a flowchart of an example technique for determining whether a distance measuring device of a materials testing system is properly calibrated.

FIG. 8 is a flowchart of an example technique 800 for determining whether a distance measuring device of a materials testing system is properly calibrated. The example technique 800 can be performed by any of a variety of appropriate computing devices, such as the computer system 104 described above with regard to FIG. 1 and/or the computer system 510 described above with regard to FIG. 5. The example technique 800 may be performed as part of the example technique 700, such as at step 706.

Information indicating one or more differences between fixed-distance spans that are part of a calibration checker can be obtained (802). Such information can be obtained in the same or similar way to how the energy characteristic information is obtained in step 702. For example, the computer system 510 can use the information reader 528 to access information 516 from the calibration checker 502, which may either directly or indirectly provide the difference information for the fixed-distance spans.

Similar to step 704, measurements for the fixed-distance spans can be received (804) and differences between the measurements of the fixed-distance spans can be determined (806). The determined differences can be compared to the obtained information that indicates the known difference values for the fixed-distance spans (808) and, based on such comparisons, a determination of the calibration of and, if appropriate, a correction factor for the distance measuring device can be determined (810). Information regarding the calibration determination and the correction factor can be output (812).

Figure 9:
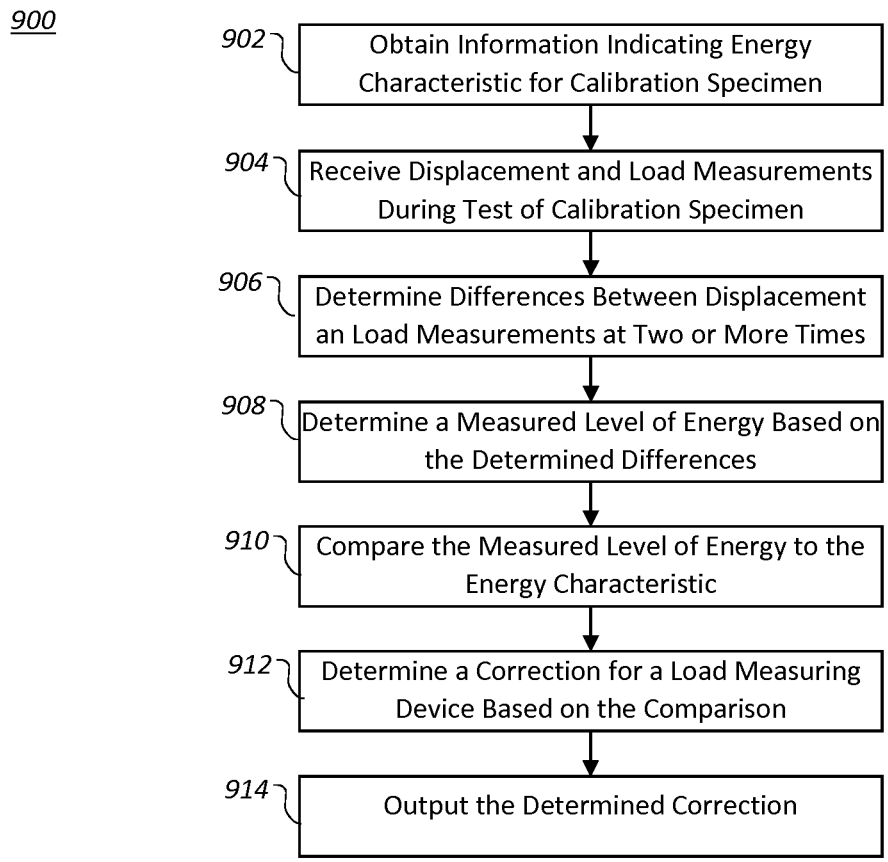
FIG. 9 is a flowchart of an example technique for determining whether a load measuring device of a materials testing system is properly calibrated.

FIG. 9 is a flowchart of an example technique 900 for determining whether a load measuring device of a materials testing system is properly calibrated. The example technique 900 can be performed by any of a variety of appropriate computing devices, such as the computer system 104 described above with regard to FIG. 1 and/or the computer system 510 described above with regard to FIG. 5. The example technique 900 may be performed as part of the example technique 700, such as at step 714, and/or in combination with the example technique 800.

Similar to step 702, information indicating energy characteristic information of a calibration specimen can be obtained (902). Displacement and load measurement made during a test of the calibration specimen can be received (904) and a determination of the differences between the displacement and load measurement as two or more times can be determined (906). For example, the computer system 510 can determine the measured change in the load on the calibration specimen 512 and the measured change in the displacement of the calibration specimen 512 during the test run by the materials testing system 504.

A measured level of energy can be determined based on the determined differences between the load and displacement measurements (908). For example, the measured energy can be determined using Equation 3 above. A comparison of the measured level of energy with the energy characteristic for the calibration specimen can be performed (910) and, based on the comparison, a determination of whether the materials testing system is properly calibrated and, if appropriate, of a correction factor for the load measuring device can be made (912). For example, the computer system 510 can compare the measured level of energy with the energy characteristic for the calibration specimen 502 and, if there is a difference of greater than a threshold amount (e.g., greater than 0.5% difference, greater than 1% difference, greater than 2% difference), a determination can be made that the load measuring device 506 is not properly calibrated. If the load measuring device 506 is determined to not be properly calibrated, the correction factor can be determined based on the comparison, such as by the percentage difference between the measured energy level and the energy characteristic (e.g., calibration factor=measured energy level/energy characteristic).

Information regarding the calibration determination and the correction factor can be output (914). For example, the computer system 510 can output such information using the output devices 518 and/or the calibration data repository 532.

Figure 10:
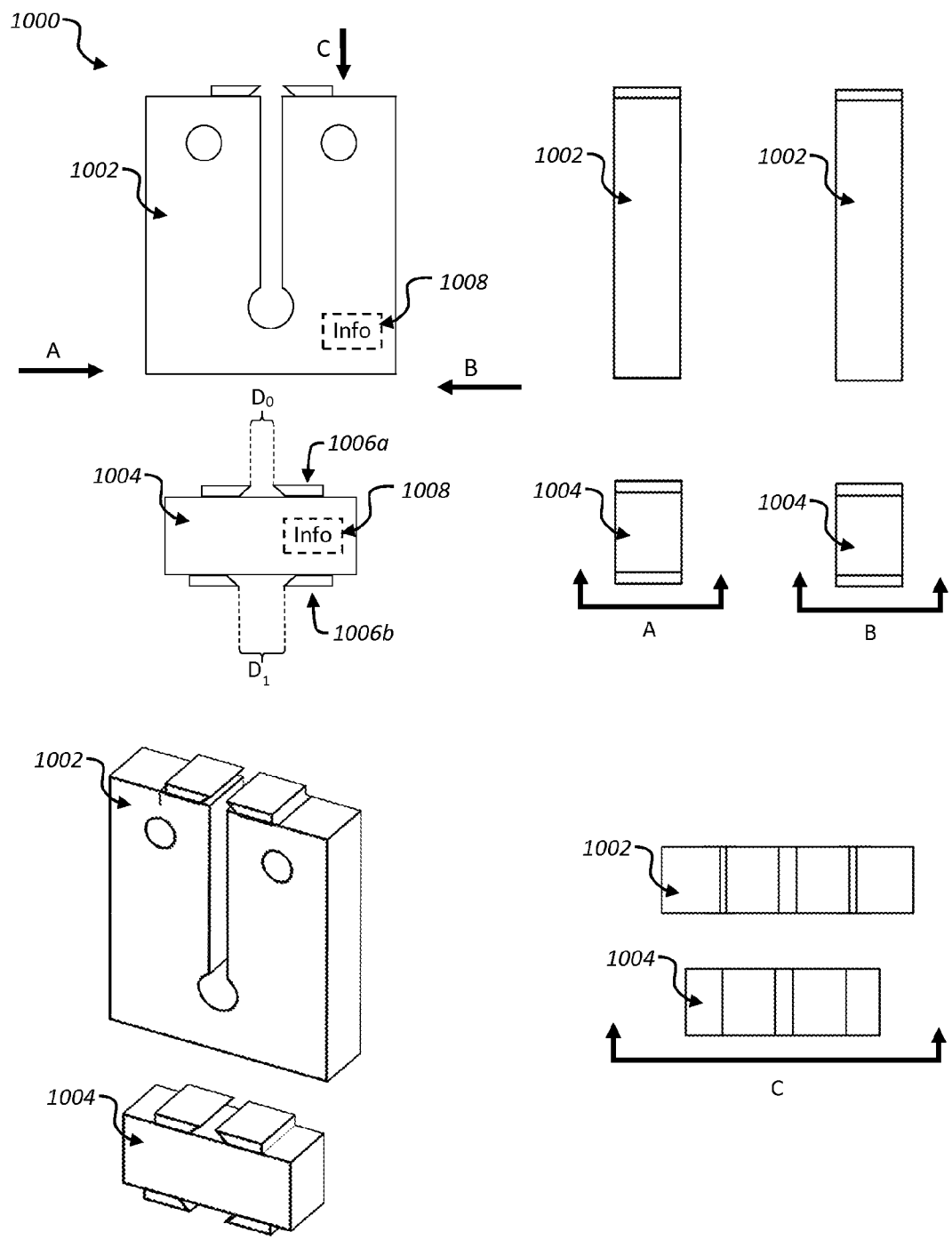
FIG. 10 depicts views of an example calibration checker.

FIG. 10 depicts view of an example calibration checker 1000. The calibration checker 1000 can be used for any and all of the systems and techniques described above, such as in the system 500 and in the techniques 700-900.

The calibration checker 1000 is similar to the calibration checkers 200 and 250, but is different from these calibration checkers in that the physical elements providing fixed-distance spans are on a physical object that is separate from the calibration specimen. For instance, the calibration checker 1000 has a calibration specimen 1002 and a separate block 1004 that includes two pairs of physical elements 1006a-b (e.g., gauge points) that define fixed distance spans. Information 1008 regarding an energy characteristic and/or differences between the distances of the fixed-distance spans can be included on one or more of the calibration specimen 1002 and the block 1004. In some implementations, the specimen 1002 may include information for the energy characteristic and the block 1004 may include information for the fixed-distance spans.

The pairs of physical elements 1006a-b can have any of a variety of appropriate configurations to provide for accurate measurements by appropriate distance measuring devices, such as contact distance measuring devices and/or non-contact distance measuring devices, as discussed above with regard to FIG. 1.

Other possible configurations are for the block 1004 are also possible. For example, the block 1004 could be a flat piece of material to which the physical elements 1006a-b are attached.

Figure 11:
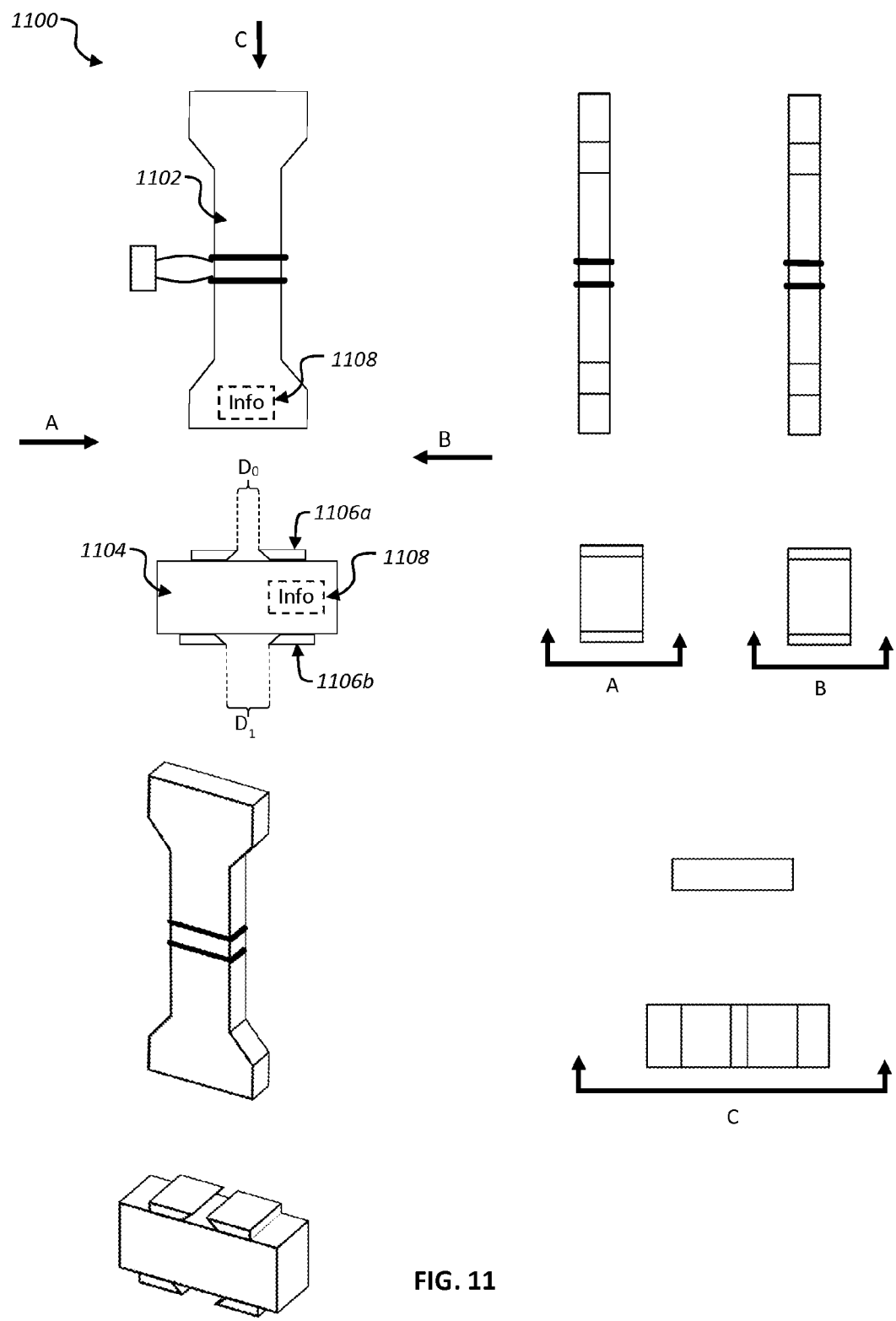
FIG. 11 depicts views of an example calibration checker.

FIG. 11 depicts view of an example calibration checker 1100. The calibration checker 1100 can be used for any and all of the systems and techniques described above, such as in the system 500 and in the techniques 700-900.

Although not drawn to scale, the example calibration checker 1100 is configured for use with a tensile strength testing machine, and includes a calibration specimen 1102 and a block 1104 with fixed-distance spans 1006a-b, similar to the block 1004. Information 1108 regarding an energy characteristic and/or differences between the distances of the fixed-distance spans can be included on one or more of the calibration specimen 1102 and the block 1104. In some implementations, the specimen 1102 may include information for the energy characteristic and the block 1104 may include information for the fixed-distance spans.

The pairs of physical elements 1106a-b can have any of a variety of appropriate configurations to provide for accurate measurements by appropriate distance measuring devices, such as contact distance measuring devices and/or non-contact distance measuring devices, as discussed above with regard to FIG. 1.

Other possible configurations for calibration checkers and calibration specimens not disclosed in this document are also possible. For example, calibration checkers and specimens can be shaped and dimensioned for use with other materials testing systems, such as asphalt material properties tester (AMPT) systems, semi-circular beam tester (SCB) system, and/or any universal load and displacement materials testing systems. In another example, calibration checkers and specimens can have shapes that are different from those depicted in the figures and described above, such as shapes with corners, sidewalls, faces, and/or voids that are rounded, curved, angled, and/or asymmetrical. Regardless of the shape and dimensions for a calibration checker and/or specimen, an energy characteristic for the checker and/or specimen can be determined and provided with the checker and/or specimen to permit for calibrations of materials testing systems to be checked using the disclosed techniques.

Computer systems described in this document that may be used to implement the systems, techniques, machines, and/or apparatuses can operate as clients and/or servers, and can include one or more of a variety of appropriate computing devices, such as laptops, desktops, workstations, servers, blade servers, mainframes, mobile computing devices (e.g., PDAs, cellular telephones, smartphones, and/or other similar computing devices), computer storage devices (e.g., Universal Serial Bus (USB) flash drives, RFID storage devices, solid state hard drives, hard-disc storage devices), and/or other similar computing devices. For example, USB flash drives may store operating systems and other applications, and can include input/output components, such as wireless transmitters and/or USB connector that may be inserted into a USB port of another computing device.

Such computing devices may include one or more of the following components: processors, memory (e.g., random access memory (RAM) and/or other forms of volatile memory), storage devices (e.g., solid-state hard drive, hard disc drive, and/or other forms of non-volatile memory), high-speed interfaces connecting various components to each other (e.g., connecting one or more processors to memory and/or to high-speed expansion ports), and/or low speed interfaces connecting various components to each other (e.g., connecting one or more processors to a low speed bus and/or storage devices). Such components can be interconnected using various busses, and may be mounted across one or more motherboards that are communicatively connected to each other, or in other appropriate manners. In some implementations, computing devices can include pluralities of the components listed above, including a plurality of processors, a plurality of memories, a plurality of types of memories, a plurality of storage devices, and/or a plurality of buses. A plurality of computing devices can be connected to each other and can coordinate at least a portion of their computing resources to perform one or more operations, such as providing a multi-processor computer system, a computer server system, and/or a cloud-based computer system.

Processors can process instructions for execution within computing devices, including instructions stored in memory and/or on storage devices. Such processing of instructions can cause various operations to be performed, including causing visual, audible, and/or haptic information to be output by one or more input/output devices, such as a display that is configured to output graphical information, such as a graphical user interface (GUI). Processors can be implemented as a chipset of chips that include separate and/or multiple analog and digital processors. Processors may be implemented using any of a number of architectures, such as a CISC (Complex Instruction Set Computers) processor architecture, a RISC (Reduced Instruction Set Computer) processor architecture, and/or a MISC (Minimal Instruction Set Computer) processor architecture. Processors may provide, for example, coordination of other components computing devices, such as control of user interfaces, applications that are run by the devices, and wireless communication by the devices.

Memory can store information within computing devices, including instructions to be executed by one or more processors. Memory can include a volatile memory unit or units, such as synchronous RAM (e.g., double data rate synchronous dynamic random access memory (DDR SDRAM), DDR2 SDRAM, DDR3 SDRAM, DDR4 SDRAM), asynchronous RAM (e.g., fast page mode dynamic RAM (FPM DRAM), extended data out DRAM (EDO DRAM)), graphics RAM (e.g., graphics DDR4 (GDDR4), GDDR5). In some implementations, memory can include a non-volatile memory unit or units (e.g., flash memory). Memory can also be another form of computer-readable medium, such as magnetic and/or optical disks.

Storage devices can be capable of providing mass storage for computing devices and can include a computer-readable medium, such as a floppy disk device, a hard disk device, an optical disk device, a Microdrive, or a tape device, a flash memory or other similar solid state memory device, or an array of devices, including devices in a storage area network or other configurations. Computer program products can be tangibly embodied in an information carrier, such as memory, storage devices, cache memory within a processor, and/or other appropriate computer-readable medium. Computer program products may also contain instructions that, when executed by one or more computing devices, perform one or more methods or techniques, such as those described above.

High speed controllers can manage bandwidth-intensive operations for computing devices, while the low speed controllers can manage lower bandwidth-intensive operations. Such allocation of functions is exemplary only. In some implementations, a high-speed controller is coupled to memory, display 616 (e.g., through a graphics processor or accelerator), and to high-speed expansion ports, which may accept various expansion cards; and a low-speed controller is coupled to one or more storage devices and low-speed expansion ports, which may include various communication ports (e.g., USB, Bluetooth, Ethernet, wireless Ethernet) that may be coupled to one or more input/output devices, such as keyboards, pointing devices (e.g., mouse, touchpad, track ball), printers, scanners, copiers, digital cameras, microphones, displays, haptic devices, and/or networking devices such as switches and/or routers (e.g., through a network adapter).

Displays may include any of a variety of appropriate display devices, such as TFT (Thin-Film-Transistor Liquid Crystal Display) displays, OLED (Organic Light Emitting Diode) displays, touchscreen devices, presence sensing display devices, and/or other appropriate display technology. Displays can be coupled to appropriate circuitry for driving the displays to output graphical and other information to a user.

Expansion memory may also be provided and connected to computing devices through one or more expansion interfaces, which may include, for example, a SIMM (Single In Line Memory Module) card interfaces. Such expansion memory may provide extra storage space for computing devices and/or may store applications or other information that is accessible by computing devices. For example, expansion memory may include instructions to carry out and/or supplement the techniques described above, and/or may include secure information (e.g., expansion memory may include a security module and may be programmed with instructions that permit secure use on a computing device).

Computing devices may communicate wirelessly through one or more communication interfaces, which may include digital signal processing circuitry when appropriate. Communication interfaces may provide for communications under various modes or protocols, such as GSM voice calls, messaging protocols (e.g., SMS, EMS, or MMS messaging), CDMA, TDMA, PDC, WCDMA, CDMA2000, GPRS, 4G protocols (e.g., 4G LTE), and/or other appropriate protocols. Such communication may occur, for example, through one or more radio-frequency transceivers. In addition, short-range communication may occur, such as using a Bluetooth, Wi-Fi, or other such transceivers. In addition, a GPS (Global Positioning System) receiver module may provide additional navigation- and location-related wireless data to computing devices, which may be used as appropriate by applications running on computing devices.

Computing devices may also communicate audibly using one or more audio codecs, which may receive spoken information from a user and convert it to usable digital information. Such audio codecs may additionally generate audible sound for a user, such as through one or more speakers that are part of or connected to a computing device. Such sound may include sound from voice telephone calls, may include recorded sound (e.g., voice messages, music files, etc.), and may also include sound generated by applications operating on computing devices.

Various implementations of the systems, devices, and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) can include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor.

To provide for interaction with a user, the systems and techniques described here can be implemented on a computer having a display device (e.g., LCD display screen, LED display screen) for displaying information to users, a keyboard, and a pointing device (e.g., a mouse, a trackball, touchscreen) by which the user can provide input to the computer. Other kinds of devices can be used to provide for interaction with a user as well; for example, feedback provided to the user can be any form of sensory feedback (e.g., visual feedback, auditory feedback, and/or tactile feedback); and input from the user can be received in any form, including acoustic, speech, and/or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

The above description provides examples of some implementations. Other implementations that are not explicitly described above are also possible, such as implementations based on modifications and/or variations of the features described above. For example, the techniques described above may be implemented in different orders, with the inclusion of one or more additional steps, and/or with the exclusion of one or more of the identified steps. Similarly, the systems, devices, and apparatuses may include one or more additional features, may exclude one or more of the identified features, and/or include the identified features combined in a different way than presented above. Features that are described as singular may be implemented as a plurality of such features. Likewise, features that are described as a plurality may be implemented as singular instances of such features. The drawings are intended to be illustrative and may not precisely depict some implementations. Variations in sizing, placement, shapes, angles, and/or the positioning of features relative to each other are possible.

What is claimed is:

1. A method for verifying calibration of a materials testing system, the method comprising:
   obtaining first information that indicates, at least, an energy characteristic of a calibration specimen, the energy characteristic defining a relationship between force and distance for the calibration specimen, wherein the calibration specimen is comprised of a material with at least a threshold level of elasticity;
   receiving, at a computational unit, results from a test run on the calibration specimen by the materials testing system, wherein the results are based on force and distance measurements taken by the materials testing system during the test, the test applying one or more loads to the calibration specimen that are within an elastic region of the material comprising the calibration specimen;
   determining, by the computational unit, whether one or more measurement devices of the materials testing system are calibrated within a threshold tolerance based on a comparison of (i) the energy characteristic of the calibration specimen and (ii) the results of the test run on the calibration specimen by the materials testing system; and
   outputting, by the computational unit, second information that indicates whether the one or more measurement devices of the materials testing system are calibrated within the threshold tolerance.

2. The method of claim 1, wherein the one or more measurement devices includes, at least, a distance measuring device;
   wherein the first information further identifies distances for a plurality of fixed-distance spans;
   the method further comprising:
      receiving distance measurements taken by the distance measuring device for the plurality of fixed-distance spans;
      determining a correction to apply to measurements taken by the distance measuring device based on a comparison of (i) the distances for the plurality of fixed-distance spans and (ii) the distance measurements taken by the distance measuring device for the plurality of fixed-distance spans; and
      outputting the correction for the distance measuring device.

3. The method of claim 2, wherein the comparison of (i) the distances for the plurality of fixed-distance spans and (ii) the distance measurements taken by the distance measuring device for the plurality of fixed-distance spans comprises a comparison of (iii) one or more differences between the distances for the plurality of fixed-distance spans and (iv) one or more differences between the distance measurements taken by the distance measuring device for the plurality of fixed-distance spans.

4. The method of claim 2, wherein the fixed-distance spans are defined by physical elements that are affixed to or embedded within one or more surfaces of the calibration specimen.

5. The method of claim 2, wherein the distance measuring device comprises a crack mouth opening displacement (CMOD) gauge.

6. The method of claim 2, further comprising:
   adjusting, based on the correction for the distance measuring device, the results from the test run on the calibration specimen by the materials testing system to generate adjusted results;
   wherein the determination of whether the one or more measurement devices are calibrated within the threshold tolerance is based on a comparison of (i) the energy characteristic of the calibration specimen and (ii) the adjusted results.

7. The method of claim 1, wherein the test run on the calibration specimen by the materials testing system is performed while the materials testing system is in an operational mode of operation during which the materials testing system is configured to test material specimens, the operational mode being different from a calibration mode of operation during which one or more components of the materials testing system are altered from their state during the operational mode.

8. The method of claim 1, further comprising:
   determining, based on the determination of whether the one or more measurement devices of the materials testing system are calibrated within the threshold tolerance, one or more corrections to measurements made by the one or more measurement devices; and
   outputting the one or more corrections for the one or more measurement devices.

9. The method of claim 8, wherein the one or more corrections comprise one or more adjustments to force measurements that are taken by the materials testing system with regard to the load that is applied by the materials testing system.

10. The method of claim 8, further comprising:
    receiving, by the computer system, production results from a test run on a viscoelastic material by the materials testing system;
    adjusting, based on the one or more corrections, the production results to generate adjusted production results; and
    outputting, by the computer system, the adjusted production results for the viscoelastic material.

11. The method of claim 1, wherein the materials testing system comprises a machine to perform disc-shaped compact tension (DCT) tests, a load measurement device to measure loads applied to the calibration specimen by the machine, and a distance measuring device.

12. The method of claim 1, wherein the computational unit comprises a computer system.

13. An apparatus for verifying calibration of a materials testing system, the apparatus comprising:
- a calibration specimen that sized and shaped to be fitted into the materials testing system for application of one or more loads;
- a first pair of physical elements that define a first span across a portion of the calibration specimen that, as the one or more loads are applied to the calibration specimen by the materials testing system, will have a variable distance; and
- a plurality of second pairs of physical elements that define a plurality of second spans across portions of the calibration specimen that have fixed-distances.

14. The apparatus of claim 13, wherein each of the plurality of the second pairs of physical elements have distances that are distinct.

15. The apparatus of claim 13, wherein the calibration specimen is comprised of a metallic material.

16. The apparatus of claim 13, wherein the calibration specimen comprises:
- a front surface;
- a back surface that is substantially parallel to the front surface;
- first and second internal circular sidewalls that extend from the front surface to the back surface creating first and second voids that pass through the calibration specimen, the first and second voids being sized and shaped to engage testing arms for the materials testing machine;
- a top surface that is substantially perpendicular to the front and back surfaces, the top surface being bifurcated by internal linear sidewalls that are substantially perpendicular to the top surface, the front surface, and the back surface, the internal linear sidewalls extending from the front surface to the back surface creating a crack that passes from the top surface to an internal point of termination that is located between the top surface and a bottom surface; and
- a semi-circular sidewall that, at one end, engages a first of the internal linear sidewalls and, at its other end, engages a second of the internal linear sidewalls at or near the internal point of termination of the crack, the semi-circular sidewall extending perpendicularly from the front surface to the back surface to create an circular void that extends through the calibration specimen at an end of the crack;
- wherein a diameter of the circular void, a length of the crack, a bottom distance from the circular void to the bottom surface, and a width of the calibration specimen are particularly dimensioned so as to provide, within a threshold tolerance, parity between a measured percentage change in displacement and a measured percentage change in force as a load is applied to the calibration specimen by the materials testing machine.

17. A system for determining whether a materials testing system is calibrated, the system comprising:
- a calibration specimen that is sized and shaped for testing by the materials testing system, the calibration specimen being comprised of a material with at least a threshold level of elasticity; and
- a computational unit that is programmed to: i) receive results from a test run on the calibration specimen by the materials testing system, ii) determine, based on a comparison of the results and an energy characteristic for the calibration specimen, whether the materials testing system is calibrated within a threshold tolerance, and iii) output information that indicates whether the materials testing system is calibrated within the threshold tolerance,
- wherein the energy characteristic defines a relationship between force and distance for the calibration specimen.

18. The system of claim 17, the system further comprising:
- a plurality of pairs of physical elements that define a plurality of fixed-distance spans;
- wherein the computational unit is further programmed to determine a correction to apply to measurements taken by a distance measuring device of the materials testing system based on a comparison of (i) known distances for the plurality of fixed-distance spans and (ii) the distance measurements taken by the distance measuring device for the plurality of fixed-distance spans.

19. The system of claim 18, wherein the computational unit is further programmed to modify the results from the test run on the calibration specimen by the materials testing system based on the correction, and to determine of whether the materials testing system is calibrated based on the modified results.

20. The system of claim 17, wherein the computational unit comprises a computer system.

* * * * *